(12) United States Patent
Yang et al.

(10) Patent No.: US 10,702,238 B2
(45) Date of Patent: Jul. 7, 2020

(54) METHOD AND SYSTEM FOR CALIBRATING AN IMAGING SYSTEM

(71) Applicant: SHANGHAI UNITED IMAGING HEALTHCARE CO., LTD., Shanghai (CN)

(72) Inventors: Hongcheng Yang, Shanghai (CN); Supratik Bose, Houston, TX (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 395 days.

(21) Appl. No.: 15/675,667

(22) Filed: Aug. 11, 2017

(65) Prior Publication Data
US 2019/0029632 A1 Jan. 31, 2019

(30) Foreign Application Priority Data

Jul. 31, 2017 (CN) .......................... 2017 1 0640498

(51) Int. Cl.
*A61B 6/00* (2006.01)
*G01T 7/00* (2006.01)
(Continued)

(52) U.S. Cl.
CPC .............. *A61B 6/583* (2013.01); *A61B 6/547* (2013.01); *A61B 6/584* (2013.01); *A61B 6/589* (2013.01);
(Continued)

(58) Field of Classification Search
CPC ......... A61B 6/583; A61B 6/547; A61B 6/584; A61B 6/589; A61B 6/032; A61B 6/4441; A61B 6/5205; G01T 7/005; G01R 33/58
(Continued)

(56) References Cited

U.S. PATENT DOCUMENTS 6,026,315 A * 2/2000 Lenz .................... G01R 33/285
600/411
2006/0109957 A1 5/2006 Lutjens et al.
(Continued)

FOREIGN PATENT DOCUMENTS

CN 102743184 A 10/2012
CN 103006251 A 4/2013
(Continued)

OTHER PUBLICATIONS

J. Chetley Ford, et al., Estimation of CT cone-beam geometry using a novel method insensitive to phantom fabrication inaccuracy: Implications for isocenter localization accuracy, 2011, 12 Pages.
(Continued)

*Primary Examiner* — Courtney D Thomas
(74) *Attorney, Agent, or Firm* — Metis IP LLC

(57) ABSTRACT

The disclosure relates to a system and method for calibrating a medical system. The method may include one or more of the following operations. Projection data of a phantom comprising a plurality of markers may be acquired from an imaging device, at a plurality of angles of a source of the imaging device. A plurality of projection matrices of a first coordinate system relating to the phantom and a transformation matrix between the first coordinate system and a second coordinate system relating to the imaging device may be determined based on the projection data of the phantom and coordinates of the plurality of markers in the first coordinate system. A plurality of projection matrices of the second coordinate system may be determined based on the plurality of projection matrices of the first coordinate system and the transformation matrix.

20 Claims, 14 Drawing Sheets

(51) Int. Cl.
  *A61B 6/03* (2006.01)
  *G01R 33/58* (2006.01)
(52) U.S. Cl.
  CPC .............. *G01T 7/005* (2013.01); *A61B 6/032* (2013.01); *A61B 6/4441* (2013.01); *A61B 6/5205* (2013.01); *G01R 33/58* (2013.01)
(58) Field of Classification Search
  USPC ........................................................ 378/207
  See application file for complete search history.

(56) References Cited

U.S. PATENT DOCUMENTS

| | | |
|---|---|---|
| 2006/0193430 A1 | 8/2006 | Kuhn |
| 2013/0229495 A1 | 9/2013 | Bani-Hashemi et al. |
| 2014/0350381 A1 | 11/2014 | Kim |
| 2016/0073986 A1 | 3/2016 | Saito et al. |

FOREIGN PATENT DOCUMENTS

| | | |
|---|---|---|
| CN | 204520733 U | 8/2015 |
| EP | 2774537 A1 | 9/2014 |
| JP | 2014151068 A | 8/2014 |

OTHER PUBLICATIONS

Mao, Weihua et al., Development of a QA phantom and automated analysis tool for geometric quality assurance of on-board MV and kV x-ray imaging systems, 2008, 10 Pages.
Xiang Qian, Research on Geometric Calibration Method for Cone Beam CT System, Excellent Master Thesis Database, 2016, 97 pages.

\* cited by examiner

METHOD AND SYSTEM FOR CALIBRATING AN IMAGING SYSTEM

CROSS-REFERENCE OF RELATED APPLICATIONS

This application claims priority of Chinese Patent Application No. 201710640498.1, filed on Jul. 31, 2017, the contents of which are hereby incorporated by reference.

TECHNICAL FIELD

The present disclosure generally relates to a medical system, and more specifically relates to methods and systems for calibrating the Computed Tomography (CT) system or radiotherapy (RT) system.

BACKGROUND

Medical systems including an imaging system, for example, a Computed Tomography (CT) system and a radiotherapy (RT) system, for example, a LINAC, etc., may be used in medical diagnosis or treatment. A subject, such as a patient, may be scanned to obtain CT data. The gantry may rotate around the subject during the scan. The sag of one or more components of the medical system may result in deviations of the medical system from its desired position during gantry rotation. There is a need for a system and method to calibrate the medical system geometry.

SUMMARY

In a first aspect of the present disclosure, a method to calibrate geometry of a medical system is provided. The method may include one or more of the following operations. A marker coordinate in a first coordinate system of at least one marker of a phantom may be acquired. The first coordinate system may relate to the phantom including the at least one marker. For each angle of a first plurality of angles of a source of an imaging device, projection data relating to the phantom may be obtained from the imaging device when the source of the imaging device is located at the angle. A source location corresponding to the angle of the source of the imaging device and a projection matrix of the first coordinate system corresponding to the angle may be determined based on the projection data and the marker coordinate of the at least one marker of the phantom. A transformation matrix between the first coordinate system and a second coordinate system may be determined based on at least one projection matrix of a first plurality of projection matrices of the first coordinate system and the at least one corresponding source location. The first plurality of projection matrices of the first coordinate system may correspond to the first plurality of angles of the source. The second coordinate system may relate to the imaging device. A first plurality of projection matrices of the second coordinate system may be determined based on the at least one projection matrix of the first plurality of projection matrices of the first coordinate system and the determined transformation matrix. A projection matrix of the second coordinate system may correspond to an angle of the source In some embodiments, to determine the transformation matrix between the first coordinate system and the second coordinate system, the method may include one or more of the following operations. An origin coordinate of the second coordinate system in the first coordinate system and a rotation angle of the second coordinate system from the first coordinate system may be determined based on the first plurality of projection matrices of the first coordinate system and the corresponding source locations. The origin coordinate of the second coordinate system in the first coordinate system may be defined by a first displacement, a second displacement, and a third displacement from the origin of the first coordinate system. The transformation matrix between the first coordinate system and the second coordinate system may be determined based on the determined origin coordinate of the second coordinate system and the rotation angle.

In some embodiments, the first coordinate system may comprise a first axis, a second axis, and a third axis. To determine the origin coordinate of the second coordinate system in the first coordinate system and the rotation angle of the second coordinate system from the first coordinate system, the method may include one or more of the following operations. A rotation plane in the first coordinate system may be determined based on the plurality of source locations corresponding to the first plurality of angles of the source. The rotation angle of the second coordinate system from the first coordinate system may be determined based on the rotation plane. The second displacement and the third displacement of the second coordinate system from the first coordinate system may be determined based on the first plurality of projection matrices of the first coordinate system. The second displacement may be in the second axis of the first coordinate system. The third displacement may be in the third axis of the first coordinate system. The first displacement may be determined based on the second displacement, the third displacement, and the rotation plane, the first displacement being in the first axis of the first coordinate system.

In some embodiments, to determine the rotation plane in the first coordinate system, the rotation plane may be constructed by minimizing a sum of squares of the distance from the plurality of source locations corresponding to the first plurality of angles of the source, to the rotation plane.

In some embodiments, to determine the second displacement and a third displacement, the method may comprise one or more of the following operations. For each projection matrix of the first plurality of the projection matrices of the first coordinate system, a projection matrix element in the projection matrix of the first coordinate system may be determined. The projection matrix element may relate to the second displacement and the third displacement. A mean of the plurality of projection matrix elements may be determined. The second displacement and the third displacement may be determined by minimizing a sum of squares of deviations of the plurality of projection matrix elements from the mean of the plurality of projection matrix elements.

In some embodiments, the first plurality of angles of the source include a first angle of the source, a second angle of the source different from the first angle of the source, and a third angle of the source different from the first angle of the source and the second angle of the source.

In some embodiments, a first angle difference between the first angle of the source and the second angle of the source or a second angle difference between the second angle of the source and the third angle of the source may range from 0 degree to 20 degrees.

In some embodiments, the first plurality of projection matrices of the first coordinate system may include a first projection matrix corresponding to the first angle of the source, and a second projection matrix corresponding to the second angle of the source.

In some embodiments, the method may further include one or more of the following operations. A second plurality of projection matrices of the first coordinate system and a second plurality of corresponding source locations may be determined based on at least one projection matrix of the first plurality of projection matrices of the first coordinate system and the corresponding source locations. A projection matrix of the second plurality of projection matrices may correspond to a source location that in turn corresponds to an angle of a second plurality of angles of the source. At least one projection matrix of the first plurality of projection matrices of the second coordinate system may be determined based on at least one projection matrix of the second plurality of projection matrices of the first coordinate system and the determined transformation matrix.

In some embodiments, the second plurality of angles of the source includes a fourth angle of the source. The determining a second plurality of projection matrices of the first coordinate system may further comprises: determining a fourth projection matrix corresponding to a fourth angle of the source by interpolating the first projection matrix and the second projection matrix.

In some embodiments, the method may further comprise: determining the transformation matrix between the first coordinate system and a second coordinate system based further on at least one projection matrix of the second plurality of projection matrices of the first coordinate system and the at least one corresponding source location.

In some embodiments, to determine the projection matrix of the first coordinate system when the source of the imaging device is located at the angle of the source corresponding to the source location, the method may include one or more of the following operations. A projection coordinate of the at least one marker of the phantom may be determined. The third coordinate system may be an image coordinate system of the imaging device. The projection matrix of the first coordinate system may be determined based on the marker coordinate in the first coordinate system and the projection coordinate in the third coordinate system.

In some embodiments, a projection coordinate of the source in the third coordinate system may be determined based on the projection matrix of the second coordinate system.

In some embodiments, the method may further include one or more of the following operations. Projection data related to a subject may be acquired by the imaging device. The projection data related to the subject may be processed with the projection matrices of the second coordinate system to generate an image.

In some embodiments, to determine the projection matrix of the second coordinate system, the projection matrix of the first coordinate system may be multiplied with the determined transformation matrix, the determined transformation matrix may be configured to transform the first coordinate system to the second coordinate system.

In some embodiments, the method may further comprise: determining a second plurality of projection matrices of the second coordinate system based on the first plurality of projection matrices of the second coordinate system.

In a second aspect of the present disclosure, a system for calibrating a medical system is provided. The system may include at least one storage medium including a set of instructions, and at least one processor configured to communicate with the at least one storage medium. When executing the set of instructions, the at least one processor may be directed to operate one or more of the following operations. Projection data of a phantom comprising a plurality of markers may be acquired from an imaging device, at a plurality of angles of a source of the imaging device. A plurality of projection matrices of a first coordinate system and a transformation matrix between the first coordinate system and a second coordinate system may be determined based on the projection data of the phantom and coordinates of the plurality of markers in the first coordinate system. An angle of the source may correspond to a projection matrix of the first coordinate system, the first coordinate system may relate to the phantom. The second coordinate system may relate to the imaging device. A plurality of projection matrices of the second coordinate system may be determined based on the plurality of projection matrices of the first coordinate system and the transformation matrix between the first coordinate system and a second coordinate system. A projection matrix of the second coordinate system may correspond to an angle of the source. The plurality of the determined projection matrices of the second coordinate system may be stored as an electronic file.

In some embodiments, the at least one processor may be further configured to determine a projection coordinate of the source in a third coordinate system based on the plurality of projection matrices of the second coordinate system. The third coordinate system may be an image coordinate system of the imaging device.

In some embodiments, the at least one processor may be further configured to operate one or more of the following operations. A plurality of source locations may be determined based on the projection data of the phantom and the coordinates of the markers in the first coordinate system. A source location may correspond to an angle of the source. An origin coordinate of the second coordinate system in the first coordinate system and a rotation angle of the second coordinate system from the first coordinate system may be determined based on the plurality of projection matrices of the first coordinate system and the corresponding source locations. The origin coordinate of the second coordinate system in the first coordinate system may be defined by a first displacement, a second displacement, and a third displacement from the origin of the first coordinate system. The transformation matrix between the first coordinate system and the second coordinate system may be determined based on the determined origin coordinate of the second coordinate system and the rotation angle.

In some embodiments, the at least one processor may be further configured to operate one or more of the following operations. A rotation plane in the first coordinate system may be determined based on the plurality of source locations. The rotation angle of the second coordinate system from the first coordinate system may be determined based on the rotation plane. The second displacement and the third displacement of the second coordinate system from the first coordinate system may be determined based on the plurality of projection matrices of the first coordinate system. The second displacement may be in the second axis of the first coordinate system. The third displacement may be in the third axis of the first coordinate system. The first displacement may be determined based on the second displacement, the third displacement, and the rotation plane. The first displacement may be in the first axis of the first coordinate system.

In some embodiments, the at least one processor may be further configured to generate projection matrices corresponding to equally-spaced angles of the source based on a plurality of projection matrices corresponding to unequally-spaced angles of the source.

In a third aspect of the present disclosure, a non-transitory computer readable medium is provided. The non-transitory computer readable medium may include executable instructions that, when executed by at least one processor, cause the at least one processor to effectuate a method comprising one or more of the following operations. A marker coordinate in a first coordinate system of at least one marker of a phantom may be acquired. The first coordinate system may relate to the phantom including the at least one marker. For each angle of a first plurality of angles of a source of an imaging device, projection data relating to the phantom may be obtained from the imaging device when the source of the imaging device is located at the angle. A source location corresponding to the angle of the source of the imaging device and a projection matrix of the first coordinate system corresponding to the angle may be determined based on the projection data and the marker coordinate of the at least one marker of the phantom. A transformation matrix between the first coordinate system and a second coordinate system may be determined based on at least one projection matrix of a first plurality of projection matrices of the first coordinate system and the corresponding source location. The first plurality of projection matrices of the first coordinate system may correspond to the first plurality of angles of the source. The second coordinate system may relate to the imaging device. A first plurality of projection matrices of the second coordinate system may be determined based on the at least one projection matrix of the first plurality of projection matrices of the first coordinate system and the determined transformation matrix. A projection matrix of the second coordinate system may correspond to an angle of the source In a fourth aspect of the present disclosure, a system having at least one processor and storage is provided. The system may include an acquisition module, a projection matrix module, and a storage. The acquisition module may be configured to acquire, from an imaging device, projection data of a phantom comprising a plurality of markers at a plurality of angles of a source of the imaging device. The projection matrix module may be configured to operate one or more of the following operations. A plurality of projection matrices of a first coordinate system and a transformation matrix between the first coordinate system and a second coordinate system may be determined based on the projection data of the phantom and coordinates of the plurality of markers in the first coordinate system. An angle of the source may correspond to a projection matrix of the first coordinate system, the first coordinate system may relate to the phantom. The second coordinate system may relate to the imaging device. A plurality of projection matrices of the second coordinate system may be determined based on the plurality of projection matrices of the first coordinate system and the transformation matrix between the first coordinate system and a second coordinate system. A projection matrix of the second coordinate system may correspond to an angle of the source. The storage may be configured to store the plurality of the determined projection matrices of the second coordinate system as an electronic file.

In some embodiments, the projection matrix module may be further configured to determine a projection coordinate of the source in a third coordinate system based on the plurality of projection matrices of the second coordinate system. The third coordinate system may be an image coordinate system of the imaging device.

In some embodiments, the projection matrix module may be further configured to operate one or more of the following operations. A plurality of source locations may be determined based on the projection data of the phantom and the coordinates of the markers in the first coordinate system. A source location may correspond to an angle of the source. An origin coordinate of the second coordinate system in the first coordinate system and a rotation angle of the second coordinate system from the first coordinate system may be determined based on the plurality of projection matrices of the first coordinate system and the corresponding source locations. The origin coordinate of the second coordinate system in the first coordinate system may be defined by a first displacement, a second displacement, and a third displacement from the origin of the first coordinate system. The transformation matrix between the first coordinate system and the second coordinate system may be determined based on the determined origin coordinate of the second coordinate system and the rotation angle.

In some embodiments, the projection matrix module may be further configured to operate one or more of the following operations. A rotation plane in the first coordinate system may be determined based on the plurality of source locations. The rotation angle of the second coordinate system from the first coordinate system may be determined based on the rotation plane. The second displacement and the third displacement of the second coordinate system from the first coordinate system may be determined based on the plurality of projection matrices of the first coordinate system. The second displacement may be in the second axis of the first coordinate system. The third displacement may be in the third axis of the first coordinate system. The first displacement may be determined based on the second displacement, the third displacement, and the rotation plane. The first displacement may be in the first axis of the first coordinate system.

In some embodiments, the projection matrix module may be further configured to generate projection matrices corresponding to equally-spaced angles of the source based on a plurality of projection matrices corresponding to unequally-spaced angles of the source.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in descending order. However, the terms may be displaced by other expression if they achieve the same purpose.

Figure 2:
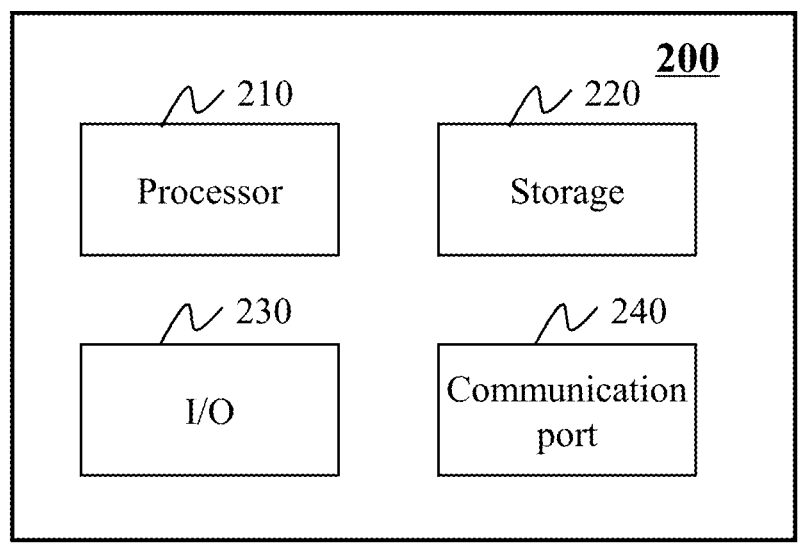
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging and/or medical treatment. In some embodiments, the medical system may include an imaging system. The imaging system may include a computed tomography (CT) system, a single photon emission computed tomography (SPECT) system, a multi-modality system, or the like, or any combination thereof. An exemplary CT system may include a cone beam computed tomography (CBCT) system. Exemplary multi-modality system may include a computed tomography-positron emission tomography (CT-PET) system, a computed tomography-magnetic resonance imaging (CT-MRI) system, etc. In some embodiments, the medical system may include a treatment system. The treatment system may include a LINAC, a Co-60 gamma irradiator, etc. Merely by way of example, the medical system may include a CT guided radiotherapy system.

For illustration purposes and not intended to limit the scope of the present disclosure, the disclosure describes systems and methods for CT image reconstruction. The systems and methods may reconstruct a CT image based on an image reconstruction algorithm.

The term "image" used in this disclosure may refer to a 2D image, a 3D image, a 4D image, and/or any related data (e.g., CT data, radiation data corresponding to the CT data). This is not intended to limit the scope of the present disclosure. For persons having ordinary skills in the art, a certain amount of variations, changes, and/or modifications may be deducted under the guidance of the present disclosure.

The term "radiation" used herein may include a particle radiation, a photon radiation, or the like, or any combination thereof. The particle may include a positron, a neutron, a proton, an electron, a μ-meson, a heavy ion, or the like, or any combination thereof. The photon may include a gamma photon, an, a beta photon, an X-ray photon, or the like, or any combination thereof. Those variations, changes, and/or modifications do not depart from the scope of the present disclosure.

Figure 1A:
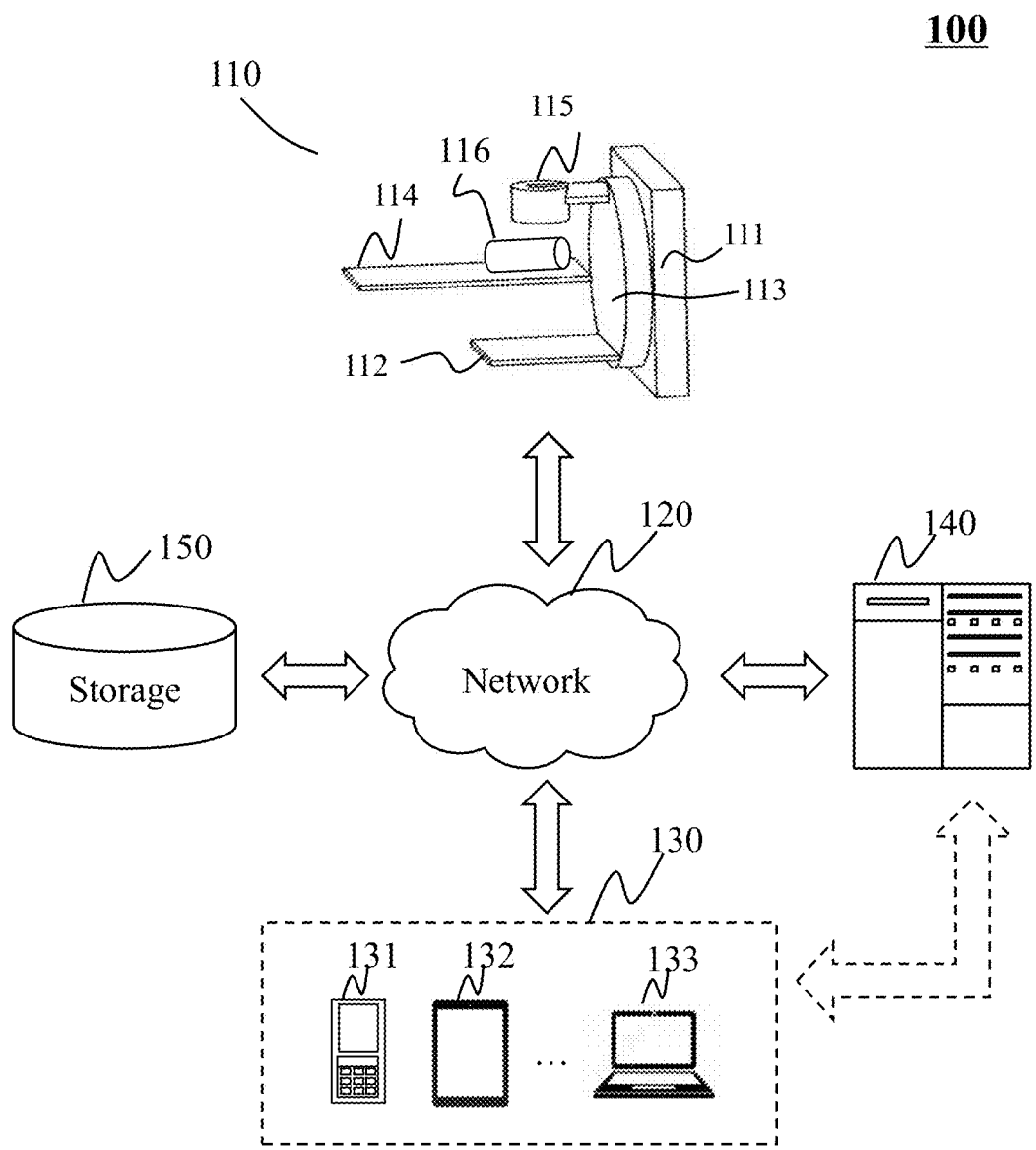
FIGS. 1A and 1B are schematic diagrams illustrating an exemplary CT system according to some embodiments of the present disclosure.
Figure 1B:
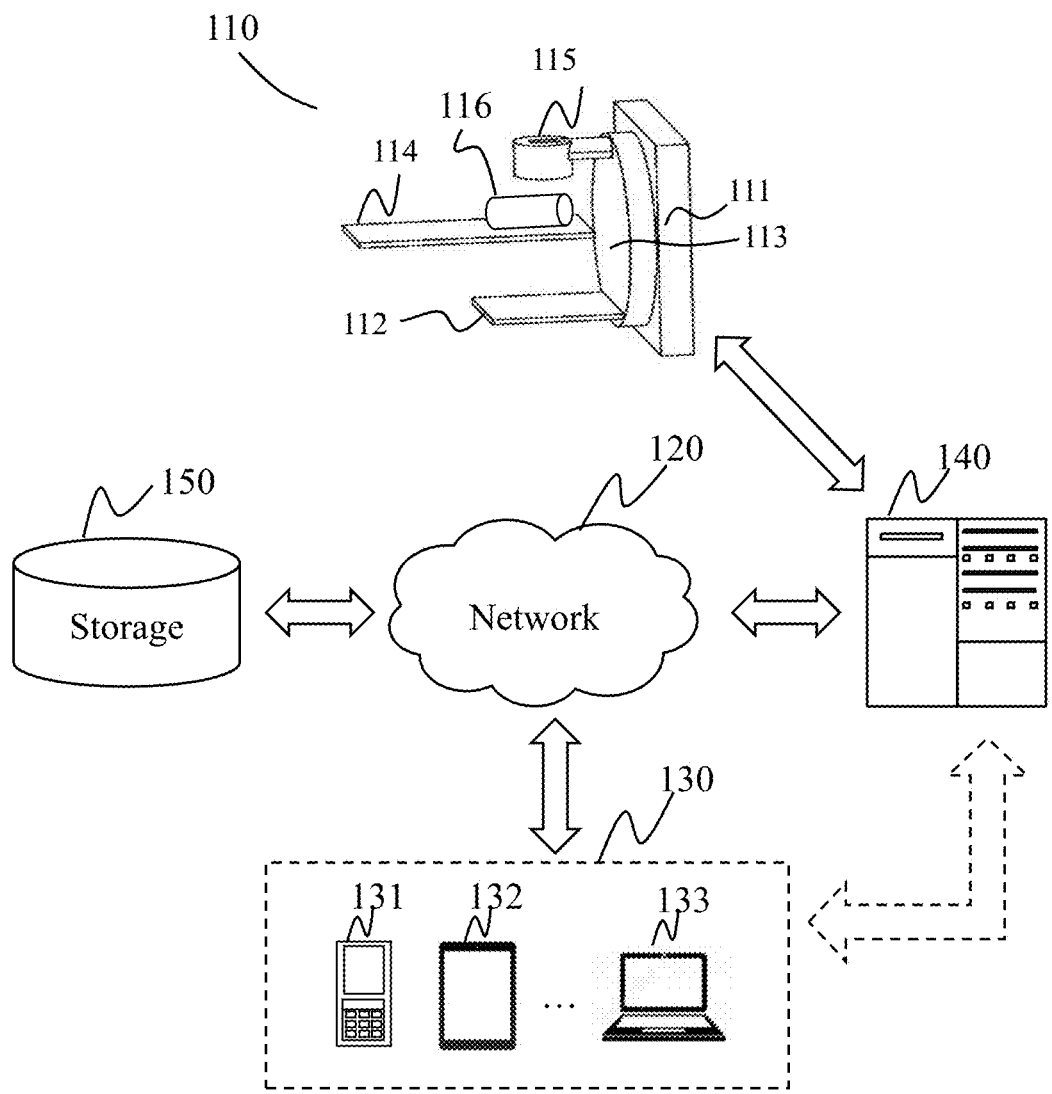

FIGS. 1A and 1B are schematic diagrams illustrating an exemplary CT system 100 according to some embodiments of the present disclosure. As shown, the CT system 100 may include a CT scanner 110, a network 120, one or more terminals 130, a processing engine 140, and a storage 150. The connection between the components in the CT system 100 may be variable. Merely by way of example, as illustrated in FIG. 1A, the CT scanner 110 may be connected to the processing engine 140 through the network 120. As another example, as illustrated in FIG. 1B, the CT scanner 110 may be connected to the processing engine 140 directly. In some embodiments, one or components in the CT system 100 may be omitted. Merely by way of example, the CT system 100 may not include the terminal(s) 130.

The CT scanner 110 may include a gantry 111, a detector 112, a detecting region 113, a table 114, and a source 115. The gantry 111 may support the detector 112 and the source 115. The source 115 is rigidly attached to the gantry 111 while the detector 112 is flexibly or rigidly attached to the gantry 111. A subject 116 may be placed on the table 114 for scanning. To perform a scan, the source 115 may emit X-rays toward the subject. At least part of the X-rays the source 115 emits may be detected by the detector 112. The subject 116 may be biological or non-biological. Merely by way of example, the subject 116 may include a patient, a man-made subject, etc. Exemplary man-made subject may include a phantom. As used herein, the phantom may refer to an object that is scanned or imaged by the CT scanner 110 to evaluate, analyze, and/or tune the imaging performance of the CT system 100.

In some embodiments, the subject 116 may include a phantom or an imaging subject. As used herein, the phantom may be scanned during a calibration scan to provide calibration data. As used herein, a calibration scan may refer to a scan in which a subject is scanned for the purposes of, e.g., calibrating the CT system 100. The calibration data may include, for example, projection data related to the phantom, the position of a plurality of markers of the phantom. As used herein, an imaging subject may refer to a subject being scanned during an imaging scan to provide imaging data. As used herein, an imaging scan may refer to a scan in which an object is scanned for e.g., imaging purposes. The imaging subject may include a patient, a man-made object, etc. Exemplary imaging data may include projection data related to the imaging subject. Calibration results may be used in subsequent imaging scans.

In some embodiments, the calibration information acquired in a calibration scan may be used to determine one or more projection matrices relating to the CT system 100. One projection matrix may correspond to one gantry angle. For example, a projection matrix relating to the CT system 100 may be determined by a calibration scan. The projection matrix relating to the CT system 100 may further be used in an imaging scan to process imaging data.

In some embodiments, the calibration data and the imaging data may be registered with a coordinate system. Merely by way of example, the position of a plurality of markers of the phantom may be registered with a coordinate system of the phantom. As another example, the projection data related to the phantom may be registered with an image coordinate system of the CT system 100. As used herein, "register" may refer to a process of assigning data with one or more coordinates in a certain coordinate system based on its position with respect to the origin of the certain coordinate system. Merely by way of example, the process of registering the position of a plurality of markers of the phantom with a coordinate system related to a phantom may refer to the process of assigning the plurality of markers with one or more coordinates in the coordinate system related to the phantom, based on the position of the plurality of markers of the phantom with respect to the origin of the coordinate system related to the phantom (e.g., the center point of the phantom).

The source 115 may emit radioactive rays (e.g., X-rays) to the subject 116. In some embodiments, the source 115 may rotate around a rotation axis, such that the subject 116 located in the detecting region 113 may be scanned from a plurality of angles of the source (or referred to as a plurality of gantry angles). Merely by way of example, the source 115 is rigidly attached to the gantry 111 while the detector 112 is rigidly or flexibly attached to the gantry 111. When the gantry 111 rotates around the rotation axis in a circular path, the source 115 and the detector 112 may rotate accordingly, and, the phantom may be scanned from a plurality of gantry angles. In some embodiments, the number of the plurality of gantry angles may be even. As used herein, an angle of the source (or referred to as a gantry angle) may relate to a position of the source of the CT scanner 110. The plurality of gantry angles may include a first gantry angle, a second gantry angle different from the first gantry angle, a third gantry angle different from the first gantry angle and the second gantry angle, etc. The first gantry angle, the second gantry angle, and the third gantry angle may be equally-spaced or unequally spaced. In some embodiments, the first gantry angle, the second gantry angle, and the third gantry angle may be equally-spaced. Merely by way of example, a first angle difference between the first gantry angle and the second angle may be the same as a second angle difference between the second gantry angle and the third angle. In some embodiments, the first angle difference and/or the second angle difference may range from 0° to 360°. In some embodiments, the first angle difference and/or the second angle difference may range from 0° to 20°. Merely by way of example, the source may scan the subject 116 at every time the gantry angle changes 1° for a total change of 360°. In some embodiments, the first gantry angle, the second gantry angle, and the third gantry angle may be unequally spaced. The first angle difference and the second angle difference may be different from each other.

The detector 112 may detect radiation (e.g., X-ray photons) emitted by the source 115. The detector 112 may be disposed opposite of the source 115. The detector 112 may extend in a direction approximately perpendicular to a central axis of the radioactive rays (e.g., X-rays) emitted from the source 115. In some embodiments, the detector 112 may rotate around the detecting region 113 together with the source 115. The detector may include a scintillation detector (e.g., a cesium iodide detector), a gas detector, etc. In some embodiments, the detector 112 may include one or more detector units. A detector unit may be arranged in a single row or multiple rows. As described in connection with the source 115, during a calibration scan, the detector 112 and the source 115 may rotate about the phantom being scanned, and, the phantom may be scanned from a plurality of gantry angles. Thus, the detector may collect projection data related to the phantom at the plurality of gantry angles.

The network 120 may include any suitable network that can facilitate exchange of information and/or data for the CT system 100. In some embodiments, one or more components of the CT system 100 (e.g., the CT scanner 110, the terminal 130, the processing engine 140, the storage 150, etc.) may communicate information and/or data with one or more other components of the CT system 100 via the network 120. For example, the processing engine 140 may obtain projection data (e.g., projection data related to a phantom) from the CT scanner 110 via the network 120. As another example, the processing engine 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the CT system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing engine 140.

The processing engine 140 may process data and/or information obtained from the CT scanner 110, the terminal 130, and/or the storage 150. The obtained data and/or information may include calibration data, imaging data, etc.

In some embodiments, the processing engine 140 may process the calibration data. As described in connection with the CT scanner 110, the calibration data may correspond to a plurality of gantry angles (e.g., a first gantry angle, a second gantry angle, a third gantry angle, etc.). In some embodiments, the processing engine 140 may process the imaging data based on the calibration data. Further, in some embodiments, the processing engine 140 may process the imaging data to generate an image.

In some embodiments, the processing engine 140 may be a single server or a server group. The server group may be centralized or distributed. In some embodiments, the processing engine 140 may be local or remote. For example, the processing engine 140 may access information and/or data stored in the CT scanner 110, the terminal 130, and/or the storage 150 via the network 120. As another example, the processing engine 140 may be directly connected to the CT scanner 110, the terminal 130 and/or the storage 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 200 having one or more components as illustrated in FIG. 2.

The storage 150 may store data, instructions, and/or any other information. In some embodiments, the storage 150 may store data obtained from the terminal 130 and/or the processing engine 140. In some embodiments, the storage 150 may store data and/or instructions that the processing engine 140 may execute or use to perform exemplary methods described in the present disclosure. In some embodiments, the storage 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the CT system 100 (e.g., the processing engine 140, the terminal 130, etc.). One or more components in the CT system 100 may access the data or instructions stored in the storage 150 via the network 120. In some embodiments, the storage 150 may be directly connected to or communicate with one or more other components in the CT system 100 (e.g., the processing engine 140, the terminal 130, etc.). In some embodiments, the storage 150 may be part of the processing engine 140.

FIG. 2 is a schematic diagram illustrating exemplary hardware and/or software components of an exemplary computing device 200 on which the processing engine 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 210 may process emission data obtained from the CT scanner 110, the terminal 130, the storage 150, and/or any other component of the CT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage 220 may store data/information obtained from the CT scanner 110, the terminal 130, the storage 150, and/or any other component of the CT system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 140 for processing projection data.

The I/O 230 may input and/or output signals, data, information, etc. In some embodiments, the I/O 230 may enable a user interaction with the processing engine 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing engine 140 and the CT scanner 110, the terminal 130, and/or the storage 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
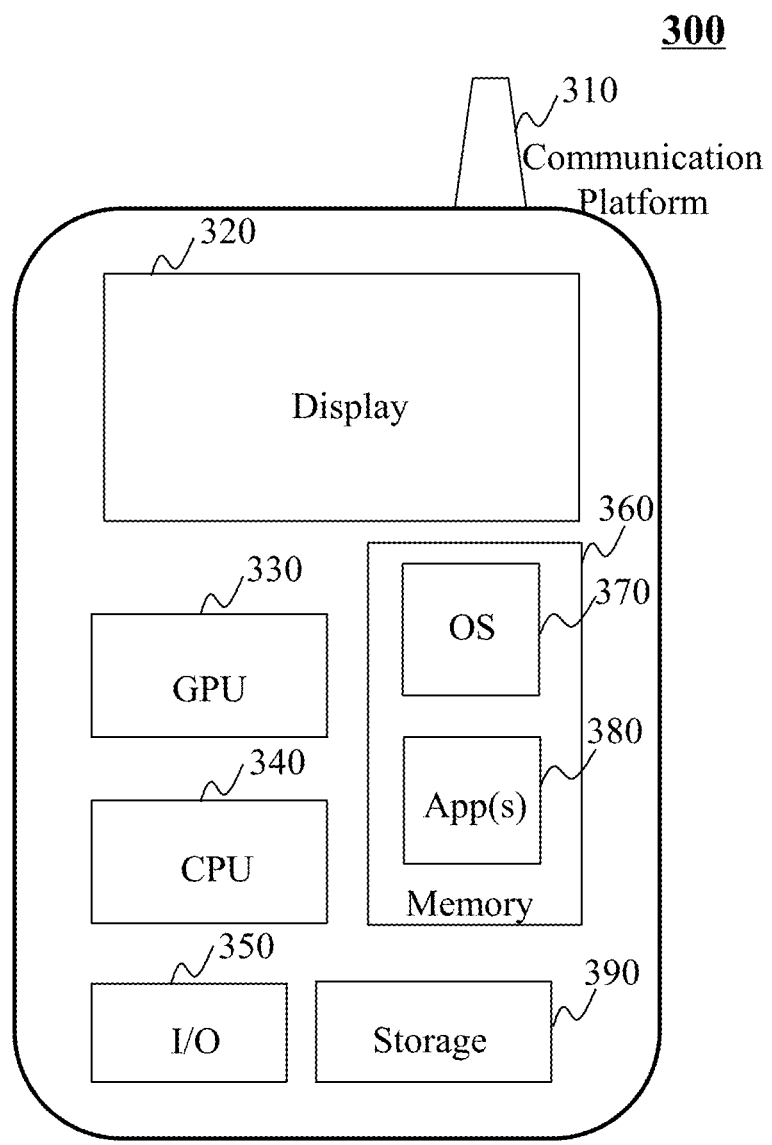
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to data processing or other information from the processing engine 140. User interactions with the information stream may be achieved via the I/O 350 and provided to the processing engine 140 and/or other components of the CT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
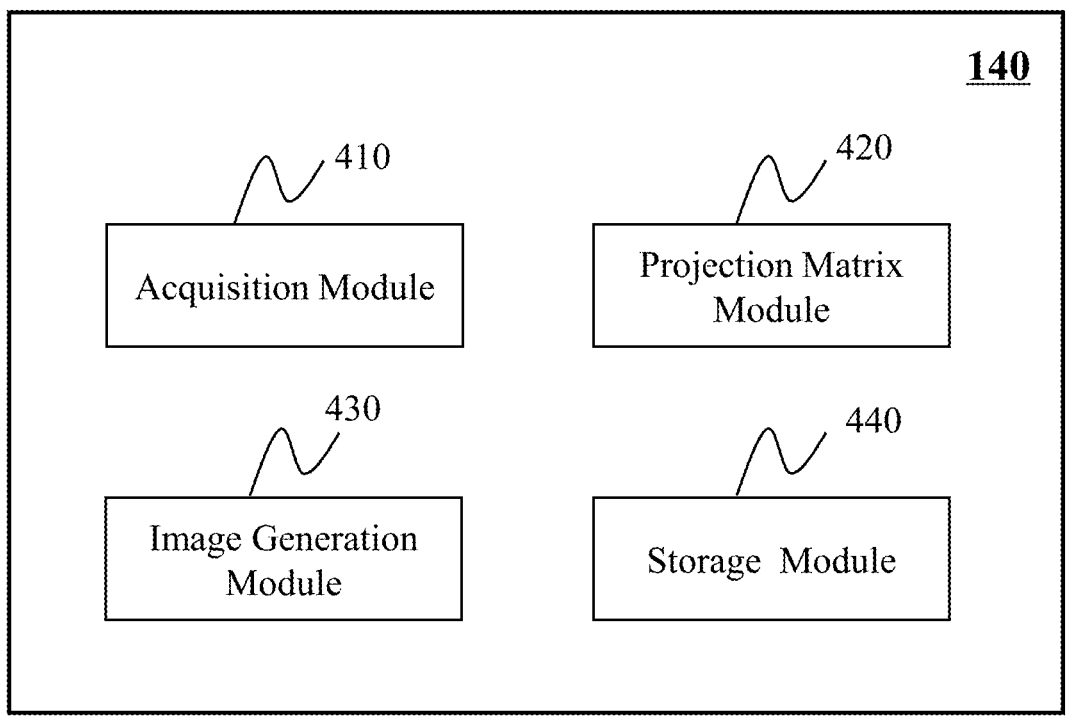
FIG. 4 is a schematic diagram illustrating an exemplary processing engine according to some embodiments of the present disclosure.

FIG. 4 is a schematic diagram illustrating an exemplary processing engine 140 according to some embodiments of the present disclosure. As illustrated in FIG. 4, the processing engine 140 may include an acquisition module 410, a projection matrix module 420, an image generation module 430, and a storage module 440.

The acquisition module 410 may acquire data from one or more components of the CT system 100 (e.g., the CT scanner 110, the terminal 130, the storage 150, etc.). The acquisition module 410 may acquire calibration data and/or imaging data. In some embodiments, the acquisition module 410 may acquire calibration data. As described in connection with the CT scanner 110, the calibration data may include projection data related to the phantom, the position of a plurality of markers of the phantom, or the like, or a combination thereof. The projection data related to the phantom may correspond to a plurality of gantry angles (e.g., a first gantry angle, a second gantry angle, a third gantry angle, etc.). In some embodiments, the acquisition module 410 may acquire imaging data.

In some embodiments, the acquisition module 410 may send the acquired data to the projection matrix module 420, the image generation module 430, and/or the storage module 440.

The projection matrix module 420 may determine a plurality of projection matrices. The plurality of projection matrices may relate to the CT system 100.

Figure 7A:
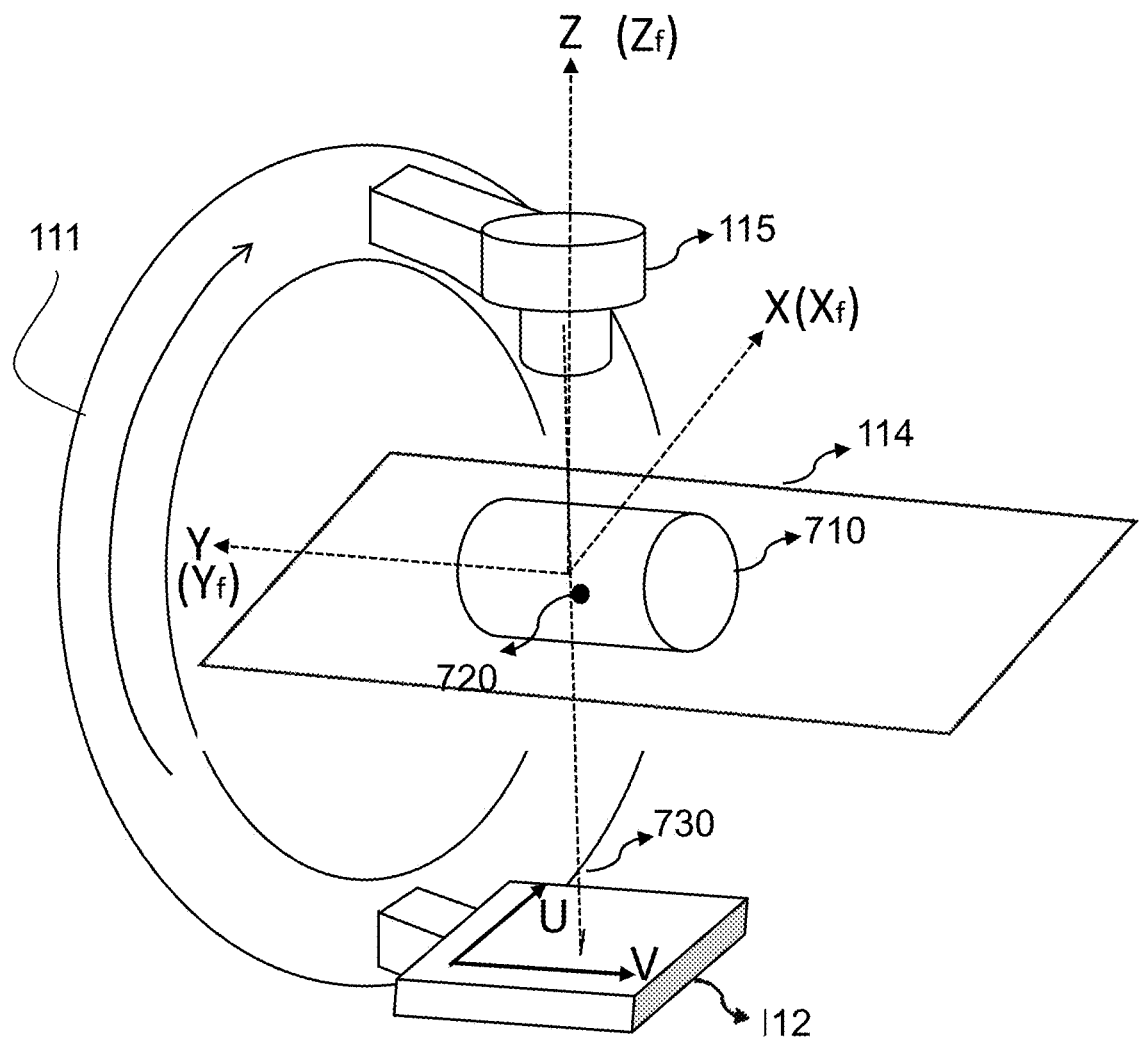
FIG. 7A illustrates a schematic diagram of an exemplary CT scanner according to some embodiments of the present disclosure.

For the determination of the plurality of projection matrices relating to the CT system 100, the projection matrix module 420 may determine one or more coordinate systems within the CT system 100. In some embodiments, the projection matrix module 420 may determine a first coordinate system based on the phantom. As used herein, the first coordinate system may also be referred to as a coordinate system of the phantom, or a phantom coordinate system. The origin of the first coordinate system may align with a specific point of the phantom. Merely by way of example, the origin of the first coordinate system may align with the center point of the phantom. In some embodiments, the first coordinate system may be a three-dimensional coordinate system (e.g., a Cartesian coordinate system). Merely by way of example, as illustrated in FIG. 7A, the first coordinate system may include a first axis (e.g., Y axis), a second axis perpendicular to the first axis (e.g., X axis), and a third axis perpendicular to the first axis and the second axis (e.g., Z axis). Specifically, the X axis and the Z axis may be in a vertical plane, the X axis and the Y axis may be in a horizontal plane, and the Y axis may be along with the center axis of the phantom. As described in connection with the CT scanner 110, the projection matrix module 420 may register the position of a plurality of markers of the phantom with the first coordinate system. Merely by way of example, the process of registering a position of the phantom with the first coordinate system may refer to the process of assigning the plurality of markers of the phantom with one or more coordinates in the first coordinate system, based on the position of the plurality of markers of the phantom with respect to the origin of the first coordinate system (e.g., the center point of the phantom).

In some embodiments, the projection matrix module 420 may determine a second coordinate system based on the CT system 100 (or the CT scanner 110). As used herein, the second coordinate system may also be referred to as a coordinate system of the CT system 100. The origin of the second coordinate system may be the intersection of the rotation plane of the source 115 and the rotation axis. In some embodiments, the second coordinate system may be an International Electrotechnical Commission (IEC) fixed coordinate system. The IEC fixed coordinate system may be a three-dimensional coordinate system. The IEC fixed coordinate system may include an $X_f$ axis, a $Y_f$ axis, and a $Z_f$ axis. The $X_f$ axis, the $Y_f$ axis, and the $Z_f$ axis may be defined according to the rotation plane and/or the rotation axis of the source 115. The rotation axis of the source 115 is normal to the rotation plane. Specifically, the rotation axis of the source 115 may be defined as $Y_f$ axis. The $X_f$ axis and the $Z_f$ axis may be in the rotation plane of the source 115. Specifically, the $Z_f$ axis may point from the center of the CT system 100 (or the origin of the second coordinate system) to the source 115, when the gantry angle is 0 degree. The $X_f$ axis may be determined according to the right handed coordinate system including the $Z_f$ axis, the $Y_f$ axis.

Figure 7B:
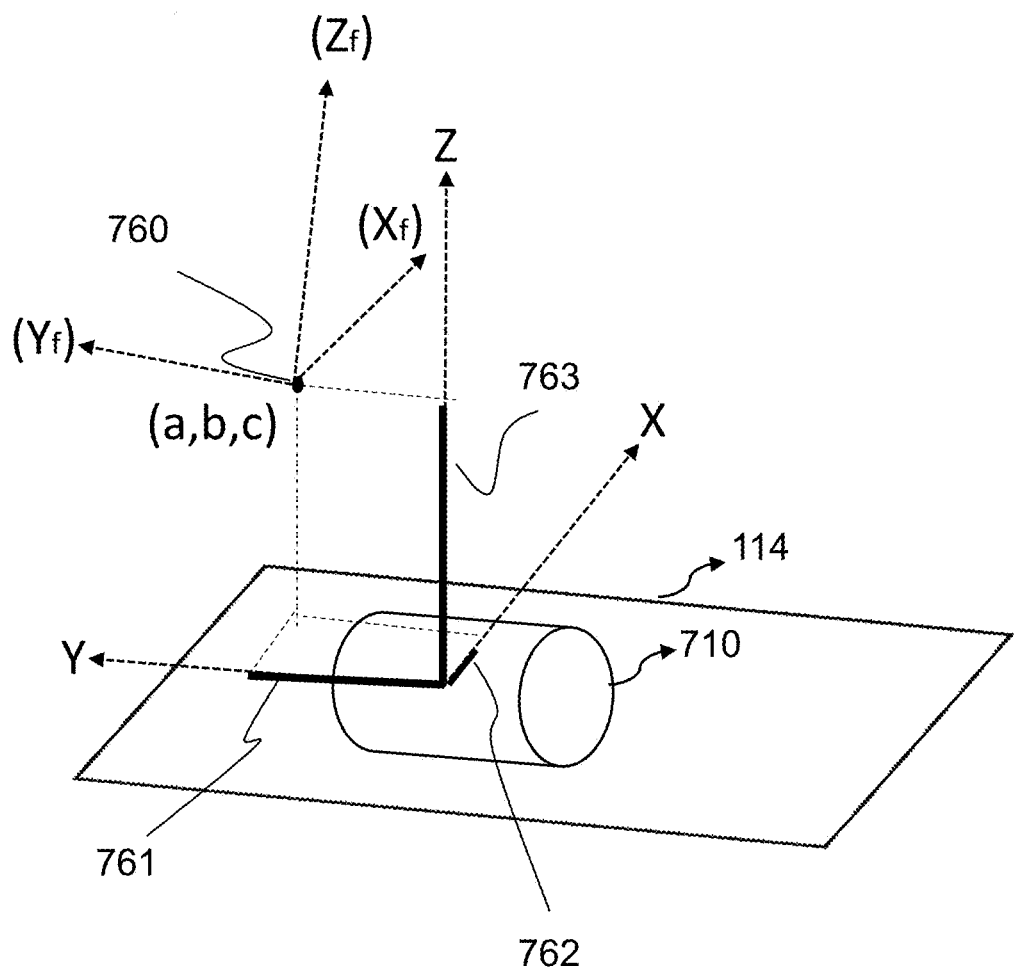
FIG. 7B illustrates a schematic diagram of a deviation of the second coordinate system from the first coordinate system according to some embodiments of the present disclosure.

In an ideal scenario, as illustrated in FIG. 7A, the $X_f$ axis and the $Z_f$ axis may be in a vertical plane, the $X_f$ axis and the $Y_f$ axis may be in a horizontal plane, and the second coordinate system may align with the first coordinate system as illustrated in FIG. 7A. In practice, as illustrated in FIG. 7B, the second coordinate system may deviate from the first coordinate system due to, for example, an improper placement of the phantom. In some embodiments, the deviation may be assessed in terms of a displacement of a point in the first coordinate system to a corresponding point in the second coordinate system. For instance, the deviation may be assessed in terms of the displacement of the origin of the second coordinate system from the origin of the first coordinate system. Merely by way of example, the displacement of the origin of the second coordinate system from the origin of first coordinate system may include a first displacement, a second displacement, and a third displacement. The first displacement may be the displacement of the origin of the second coordinate system from the origin of the first coordinate system in a first axis of the second coordinate system (e.g., the $Y_f$ axis) or in a first axis of the first coordinate system (e.g., the Y axis). The second displacement may be the displacement of the origin of the second coordinate system from the origin of the first coordinate system in a second axis of the second coordinate system (e.g., the $X_f$ axis) or in a second axis of the first coordinate system (e.g., the X axis). The third displacement may be the displacement of the origin of the second coordinate system from the origin of the first coordinate system in a third axis of the second coordinate system (e.g., the $Z_f$ axis) or in a third axis of the first coordinate system (e.g., the Z axis). In some embodiments, the deviation may be assessed in terms of a rotation angle between the first coordinate system and the second coordinate system. In some embodiments, the deviation may be assessed in terms of the displacement of a point (e.g., the origin of the second coordinate system) from a corresponding point (e.g., the origin of the first coordinate system) and the rotation angle between the first coordinate system and the second coordinate system. It should be noted that in this disclosure, the terms "deviation" and "displacement" may be used interchangeably. This is not intended to limit the scope the present disclosure.

In some embodiments, the projection matrix module 420 may determine a third coordinate system related to the detector 112. As used herein, the third coordinate system may also be referred to as an image coordinate system of the CT system 100. The origin of the third coordinate system may be a point in the detector 112. The point may be, for example, the center point of the detector 112, a top left corner point of the detector 112, a top right corner point of the detector 112, etc. The top left corner point or the top right corner point of the detector 112 may be from a view looking towards the gantry 111, i.e., the positive direction of the Y axis as illustrated in FIG. 7A. The third coordinate system may be two dimensional or three dimensional. Merely by way of example, as illustrated in FIG. 7A, the third coordinate system may be a two dimensional coordinate system defined by a U axis and a V axis. The U axis and the V axis may be parallel to the $X_f$ axis and the $Y_f$ axis, respectively. As described in connection with the CT scanner 110, the projection matrix module 420 may register projection data related to the phantom with the third coordinate system.

The projection matrix module 420 may determine the plurality of projection matrices related to the CT system 100 (e.g., the second coordinate system) based on the first coordinate system, the second coordinate system, the third coordinate system, and the calibration data (e.g., the projection data related to the phantom, the position of a plurality of markers of the phantom, etc.). Merely by way of example, the projection matrix module 420 may determine a plurality of projection matrices of the first coordinate system based on the projection data related to the phantom and the position of a plurality of markers of the phantom. The plurality of projection matrices of the first coordinate system may include a plurality of projection matrices corresponding to a plurality of gantry angles. For example, the plurality of projection matrices of the first coordinate system may include a first projection matrix of the first coordinate system corresponding to a first gantry angle, a second projection matrix of the first coordinate system corresponding to a second gantry angle, a third projection matrix of the first coordinate system corresponding to a third gantry angle, etc. In some embodiments, the first gantry angle, the second gantry angle, and the third gantry angle may be unequally-spaced. The projection matrix module 420 may generate projection matrices corresponding to equally-spaced gantry angles based on the projection matrices corresponding to the unequally-spaced gantry angles. For example, the projection matrix module 420 may determine a fourth projection matrix of the first coordinate system corresponding to a fourth gantry angle based on the first projection matrix and the second projection matrix of the first coordinate system by way of, e.g., interpolation. For instance, the fourth gantry angle, the first gantry angle, and the second gantry angle are equally-spaced.

In some embodiments, the projection matrix module 420 may determine a transformation matrix between the first coordinate system and the second coordinate system. Detailed description of the determination of the transformation may be found elsewhere in the present disclosure. See, for example, the description of the transformation determination unit 840. Further, in some embodiments, the projection matrix module 420 may determine a plurality of projection matrices of the second coordinate system based on the plurality of projection matrices of the first coordinate system and the transformation matrix. Merely by way of example, the projection matrix module 420 may determine a plurality of projection matrices of the second coordinate system by multiplying a plurality of projection matrices of the first coordinate system with the transformation matrix. The plurality of projection matrices of the second coordinate system and the plurality of projection matrices of the first coordinate system may correspond to the same plurality of gantry angles.

In some embodiments, the projection matrix module 420 may determine the beam center $(u_0, v_0)$, which may represent the projection location of the source in the third coordinate system, to be the coordinate of the detector unit on which the axis of the radiation beam emitted by the source 115 impinged on. The projection matrix module 420 may determine a projection coordinate of the source $(u_0, v_0)$ in the third coordinate system based on the projection matrix of the second coordinate system. For example, the projection matrix module 420 may determine a plurality of projection matrices of the second coordinate system (e.g., the coordinate system related to the CT system 100) based on projection data of the phantom and coordinates of a plurality of markers of the phantom in the first coordinate system (e.g., the coordinate system of the phantom). Further, the projection matrix module 420 may determine the projection coordinate of the source $(u_0, v_0)$ in the third coordinate system based on the plurality of projection matrices of the second coordinate system. It should be noted here that the plurality of projection matrices of the second coordinate system may be determined by a process other than the process illustrated in the present disclosure (e.g., FIG. 9A). This is not intended to limit the scope of the present disclosure.

In some embodiments, the projection matrix module 420 may be connected to or communicate with the image generation module 430 and/or the storage module 440.

The image generation module 430 may process data with the generated plurality of projection matrices related to the CT system 100 (e.g., the second coordinate system).

In some embodiments, the image generation module 430 may generate an image by processing the imaging data with the generated plurality of projection matrices. In some embodiments, the image generation module 430 may utilize one or more image reconstruction algorithms to generate one or more 3D images. Descriptions of exemplary image reconstruction algorithms may be found elsewhere in the present disclosure. In some embodiments, the image generation module 430 may generate a plurality of 2D images (e.g., two 2D projection images at two different angles). In some embodiments, the image generation module 430 may utilize the generated images to determine whether the positioning of the imaging subject (e.g., the patient) is accurate in an image-guided radiation treatment process. For example, the projection matrix module 420 may determine one or more source coordinates in the third coordinate system based on the projection matrices of the CT system 100 (e.g., the second coordinate system). The image generation module 430 may compare the generated images with the one or more images for the radiotherapy plan to determine whether the positioning of the imaging subject is accurate based on the source coordinates. Specifically, the image generation module 430 may determine the positioning of the imaging subject to be accurate when the generated images are the same as the corresponding images for the radiotherapy plan, or the difference between the generated images and the corresponding images for the radiotherapy plan is within a certain range.

The storage module 440 may store data and/or information. Merely by way of example, the storage module 440 may store a plurality of projection matrices and beam center relating to the CT system 100 generated by the projection matrix module 420.

It should be noted that the above description of the processing engine 140 is merely provided for the purposes of illustration, and not intended to limit the scope of the present disclosure. For persons having ordinary skills in the art, multiple variations and modifications may be made under the teaching of the present invention. However, those variations and modifications do not depart from the scope of the present disclosure. For example, the image generation module 430 may be omitted, and the CT scanner 110 and/or the terminal 130 may be configured to execute one or more functions of the image generation module 430 as described in the present disclosure.

Figure 5:
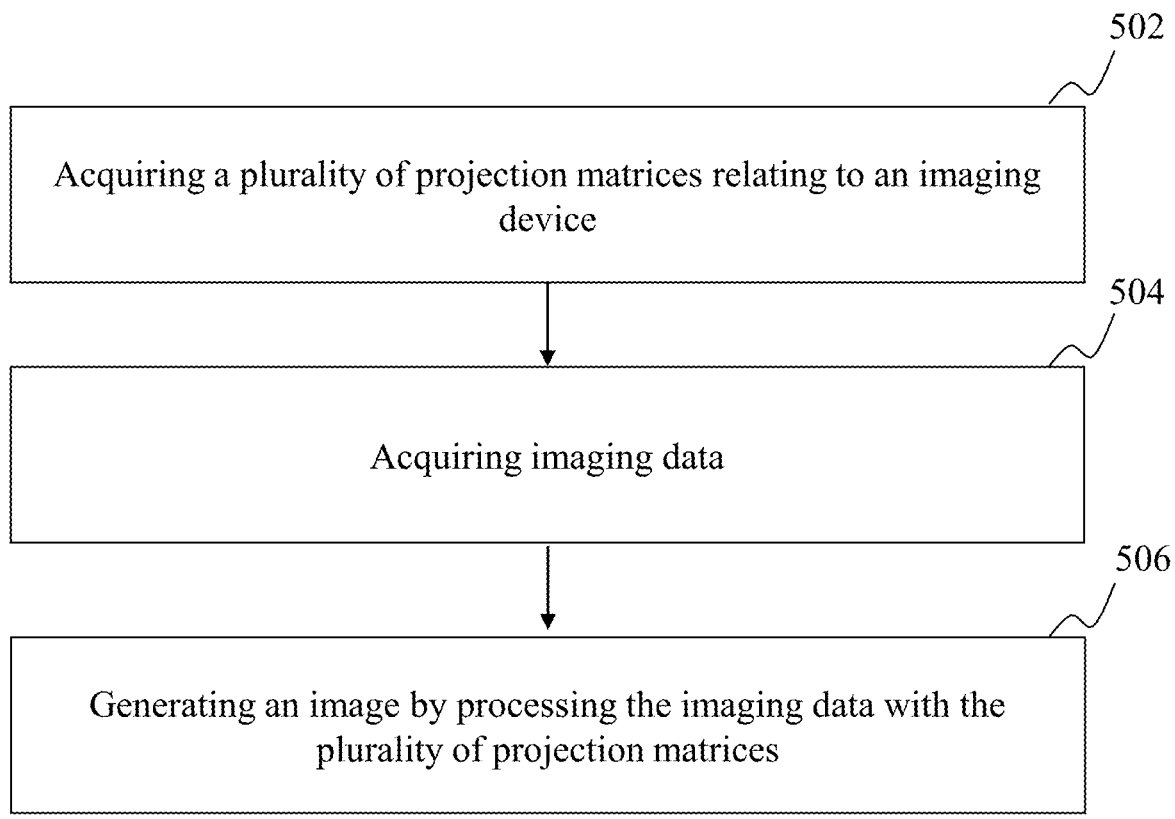
FIG. 5 is a flowchart illustrating an exemplary process for generating an image according to some embodiments of the present disclosure.

FIG. 5 is a flowchart illustrating an exemplary process 500 for generating an image according to some embodiments of the present disclosure. The process, or a portion thereof, may be implemented on a computing device as illustrated in FIG. 2 or a mobile device as illustrated in FIG. 3. For illustration purposes, the following description is provided with reference to the CT system 100 as illustrated in FIG. 1A and FIG. 1B. As already described, the CT system 100 includes the image generation module 430 (as illustrated in FIG. 4).

In 502, a plurality of projection matrices relating to an imaging device may be acquired. The plurality of projection matrices may be acquired by the image generation module 430 from the projection matrix module 420. The plurality of projection matrices may relate to the CT system 100, and may correspond to a plurality of gantry angles (e.g., a first gantry angle, a second gantry angle, a third gantry angle, etc.).

In 504, imaging data may be acquired. The acquired imaging data may include projection data related to an imaging subject. The imaging data may be acquired when the source of the CT scanner 110 is at one or more of the plurality of gantry angles corresponding to the calibration data (e.g., the first gantry angle, the second gantry angle, the third gantry angle, etc.).

In 506, an image may be generated by processing the imaging data with the plurality of projection matrices. In some embodiments, a 3D image may be generated by utilizing an image generation algorithm. Exemplary image generation algorithm may be illustrated elsewhere in the present disclosure. A plurality of 2D images may be generated, which may further be used to determine whether the position of the imaging subject (e.g., the patient) is accurate, in an image-guided radiation treatment process.

It should be noted that the flowchart described above is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, an operation in which the calibration data and/or the imaging data may be stored may be added to the process 500.

Figure 6A:
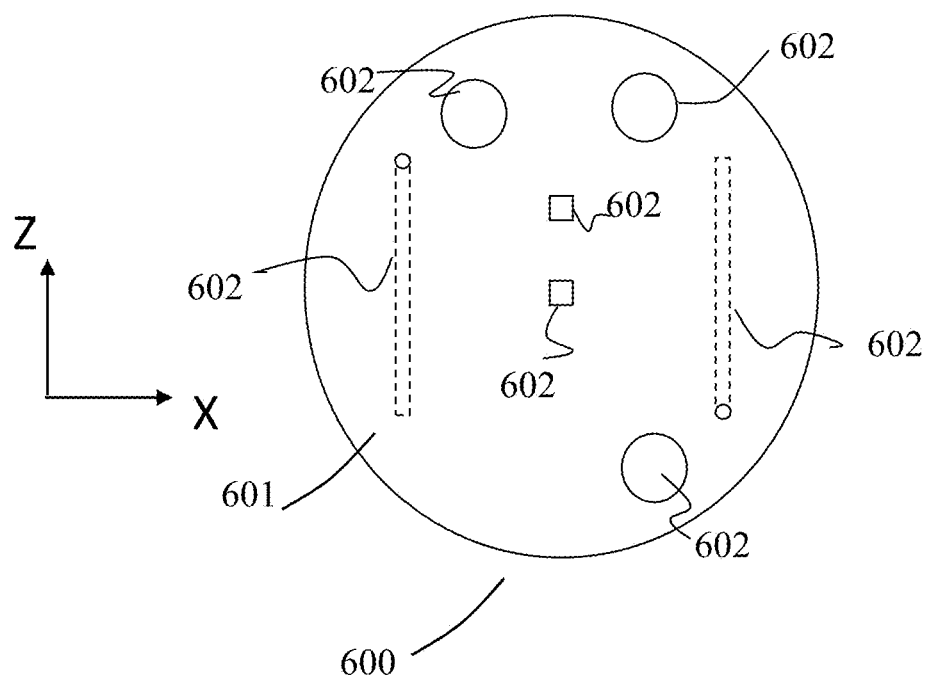
FIG. 6A is a schematic diagram illustrating a cross-sectional view of an exemplary phantom according to some embodiments of the present disclosure.
Figure 6B:
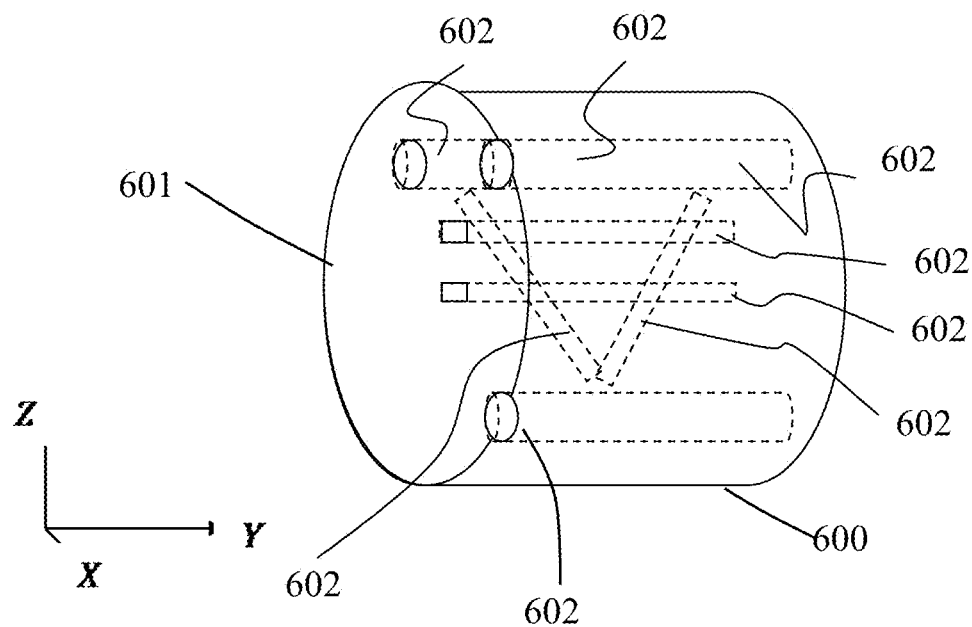
FIG. 6B is a schematic diagram illustrating a perspective view of the exemplary phantom according to some embodiments of the present disclosure.

FIG. 6A is a schematic diagram illustrating a cross-sectional view of an exemplary phantom (a phantom 600) according to some embodiments of the present disclosure. FIG. 6B is a schematic diagram illustrating a perspective view of the phantom 600 illustrated by FIG. 6A according to some embodiments of the present disclosure. As illustrated in FIG. 6A and/or FIG. 6B. The phantom 600 may include a body 601 and one or more markers 602. The marker(s) 602 may be used for the imaging performance analysis.

The marker(s) 602 may be used for analyzing imaging performance of the CT system 100. The material, shape, size, and orientation of a marker 602 may be selected based on a specific imaging parameter that the marker 602 is used for analyzing. Exemplary mental materials suitable for a marker 602 include tungsten, steel, or the like, or a combination thereof. Exemplary shapes suitable for a marker 602 include sphere, wire, with various cross-sectional shapes, or the like, or a combination thereof. Exemplary orientations suitable for a marker 602 include vertical, horizontal, tilted, etc. It may take one or more markers 602 to analyze one aspect of the imaging performance. For example, it may take a set of, e.g., 4 markers 602 to analyze the linearity of the CT scanner 110. As another example, it may take at least eight markers 602 to determine a projection matrix relating to the CT system 100.

The body 601 may provide mechanical support to the marker(s) 602. A marker 602 may be embedded or enclosed in the body 601. Compared to the marker 602, the body 601 may have none, negligible, or reduced signal in response to the X-rays emitted by the source of the scanner being analyzed, and thus the marker 602 may be distinguished from the body 601 in a CT image of the phantom 600. In some embodiments, the body 601 may be made of a low density material, such as, delrin, polystyrene, etc. The marker 602 may be made of a high density material, such as, tungsten, steel, etc. The body 601 may be a disk-like or column-like object. The cross-section of the body 601 may be a circle, a square, a rectangle, an oval, or any other proper shape. The body 601 may be solid or hollow. In some embodiments, besides the markers 602, the body 601 may include other components or modules for various purposes. For example, the body 601 may include a housing for protecting the phantom 600 or a portion thereof, and/or for fixing the phantom 600 onto the table 114. In some embodiments, the markers 602 may be spirally distributed in the body 601, or consists of two symmetrical circles in the body 601. It should be noted that the above structure of the phantom 600 is provided for illustration purposes, and is not intended to limit the scope of the present disclosure.

It may be noticed that, the drawings of phantom 600 illustrated in FIG. 6 and the related description are only for demonstration purposes, and is not intend to apply a limitation to the appearance, number, type, structure, material, function, or usage of the phantom 600, or a portion thereof including, for example, the body 601, or the marker 602.

FIG. 7A illustrates a schematic diagram of an exemplary CT scanner 110 according to some embodiments of the present disclosure. As illustrated in FIG. 7A, the CT scanner 110 may include a gantry 111, a detector 112, a table 114, and a source 115. The gantry 111 may support the detector 112 and the source 115. A phantom 710 may be placed on the table 114 for scanning. In some embodiments, the position at which the phantom 710 is placed on the table 114 may be determined based on light field crosshair or laser. Merely by way of example, the phantom 710 is placed at a position to align the center of crosshair on the surface of the phantom 710 with the center of the light field crosshair or the laser. In some embodiments (not shown in FIG. 7A), there are a plurality of crosshairs on the surface of the phantom 710, according to which the origin of the coordinate system of the phantom (e.g., the first coordinate system) may be determined. In some embodiments, the phantom 710 may further be fixed on the table 114 at the determined position.

The source 115 may emit radioactive rays (e.g., X-rays) 730 passing through a marker 720 of the phantom 710, generating projection data related to the phantom 710. In some embodiments, the projection data may be detected by the detector 112.

In some embodiments, the source 115 may rotate about a rotation axis to be positioned at various gantry angles, such that phantom 710 located in the detecting region 113 may be scanned from a plurality of directions. Merely by way of example, the source 115 and the detector 112 may be movably or fixedly attached to the gantry 111. When the gantry rotates around the rotation axis in a circular path, the source 115 and the detector 112 may rotate accordingly, and the phantom 710 may be scanned from a plurality of gantry angles. As used herein, the gantry angle may relate to the position of the source 115 with reference to the CT scanner 110. For example, the gantry angle may be the angle between the central axis of the radioactive rays (e.g., X-rays) 730 and the $Z_f$ axis of the CT scanner 110. Merely by way of example, as illustrated in FIG. 7A, the phantom 710 is scanned from a gantry angle of 0°.

In some embodiments, a first coordinate system may be determined based on the phantom 710. The origin of the first coordinate system may align with the center point of the phantom 710. The first coordinate system may be defined by an X axis, a Y axis, and a Z axis. Specifically, the X axis and the Z axis may be in a vertical plane, the X axis and the Y axis may be in a horizontal plane, the Y axis may be along the center axis of the phantom 710.

In some embodiments, a second coordinate system may be determined based on the CT system 100 (or the CT scanner 110). The origin of the second coordinate system may be the intersection of the rotation plane and the rotation axis. The second coordinate system may be an International Electrotechnical Commission (IEC) fixed coordinate system. As illustrated in FIG. 7A, the second coordinate system may include an $X_f$ axis, a $Y_f$ axis, and a $Z_f$ axis. The rotation axis of the rotation source (or referred to as the source) 115 may be defined as the $Y_f$ axis. The $X_f$ axis and the $Z_f$ axis may be in a vertical plane, the $X_f$ axis and the $Y_f$ axis may be in a horizontal plane. The $Z_f$ axis may point from the center of the CT system 100 (or the origin of the second coordinate system) to the source 115, when the gantry angle is 0 degree. The $X_f$ axis may be determined according to the right handed coordinate system including the $Z_f$ axis, the $Y_f$ axis. In an ideal scenario, the second coordinate system may align with the first coordinate system as illustrated in FIG. 7A, and the origin of the second coordinate system may coincide with the origin of the first coordinate system.

In some embodiments, a third coordinate system related to the detector 112 may be determined. The origin may be, for example, a top left corner point of the detector 112. The top left corner point of the detector 112 may be from a view of looking towards the gantry. The third coordinate system may be a two dimensional coordinate system defined by a U axis and a V axis. For instance, the U axis and the V axis may be parallel to the $X_f$ axis and the inversely $Y_f$ axis of the second coordinate system, respectively.

FIG. 7B illustrates a schematic diagram of a deviation of the second coordinate system from the first coordinate system according to some embodiments of the present disclosure. The first coordinate system may relate to the phantom 710 placed on the table 114. The first coordinate system may be defined by the X axis, the Y axis, and the Z axis. The second coordinate system may be defined by the $X_f$ axis, the $Y_f$ axis, and the $Z_f$ axis. The deviation of the second coordinate system from the first coordinate system may include a displacement and/or a rotation angle. As illustrated in FIG. 7B, the origin of the second coordinate system 760 in the first coordinate system may be expressed as (a,b,c), wherein a may represent the first displacement 761, b may represent the second displacement 762, and c may represent the third displacement 763. The angle between the X axis and the $X_f$ axis may represent the first rotation angle. The angle between the Y axis and the $Y_f$ axis may represent the second rotation angle. The angle between the Z axis and the $Z_f$ axis may represent the third rotation angle.

Figure 8:
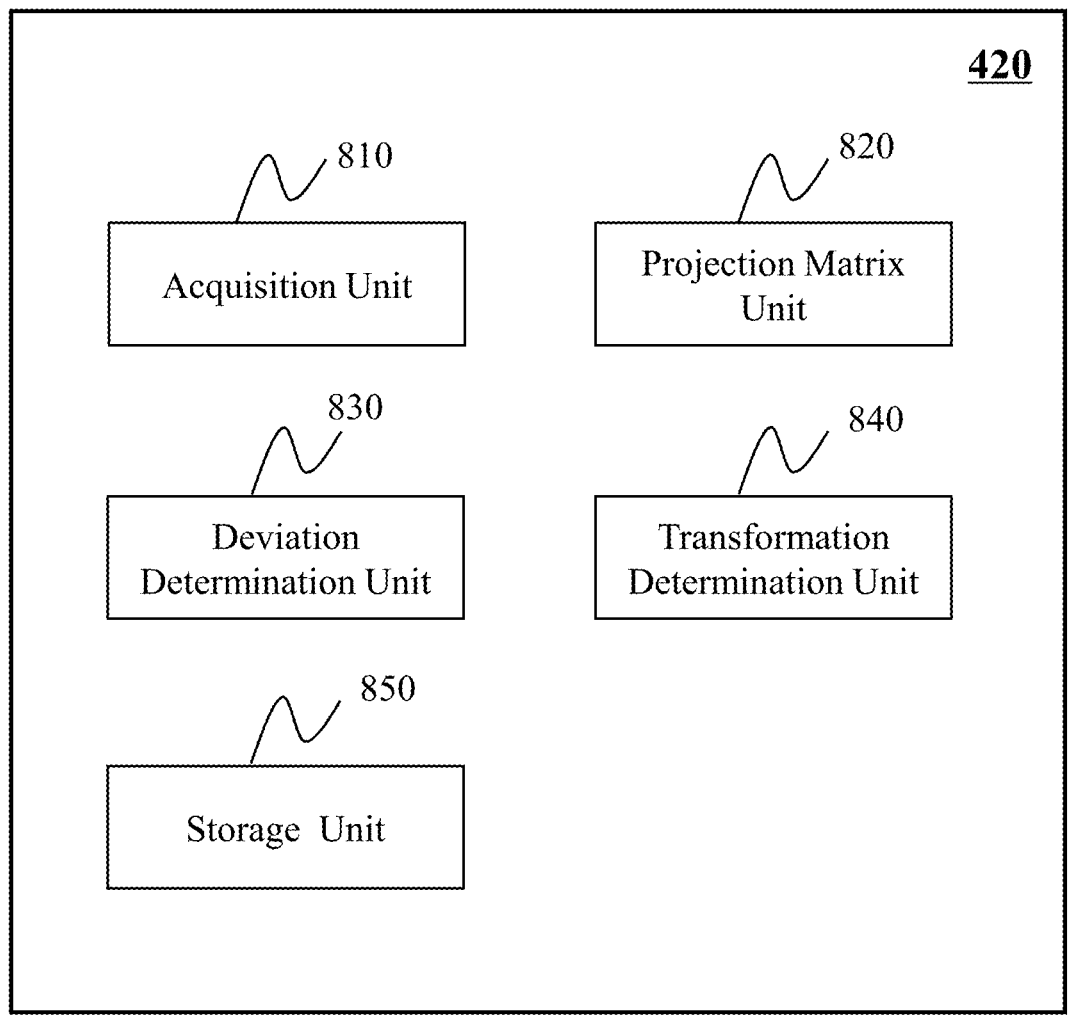
FIG. 8 is a block diagram illustrating an exemplary projection matrix module according to some embodiments of the present disclosure.

FIG. 8 is a block diagram illustrating an exemplary projection matrix module 420 according to some embodiments of the present disclosure. As illustrated in FIG. 8, the projection matrix module 420 may include an acquisition unit 810, a projection matrix unit 820, a deviation determination unit 830, a transformation determination unit 840, and a storage unit 850. The projection matrix module 420, or a portion thereof, may be implemented on a computing device as illustrated in FIG. 2, or a mobile device as illustrated in FIG. 3.

The acquisition unit 810 may acquire calibration data (e.g., projection data related to a phantom, positions of a plurality of markers of a phantom, etc.). Merely by way of example, the acquisition unit 810 may acquire calibration data from the CT scanner 110 or from a storage device (e.g., the storage module 440, the storage 150, the storage 220, memory 360, and a storage 390, etc.).

The acquisition unit 810 may register the calibration data with a coordinate system. For example, the acquisition unit 810 may register e.g., a position of a plurality of markers of the phantom with the first coordinate system, to determine a coordinate of the plurality of markers in the first coordinate system. Detailed description of the registering position of the plurality of markers of the phantom may be found elsewhere in the present disclosure. As another example, the acquisition unit 810 may register projection data related to the plurality of markers with the third coordinate system relating to the detector 112 to determine a projection coordinate of the plurality of markers in the third coordinate system. Specifically, for example, the process of registering the projection data related to the plurality of markers with the third coordinate system may refer to the process of assigning the projection data with one or more coordinates in the third coordinate system, based on the position of the projection data (e.g., the corresponding position on the detector 112) with respect to the origin of the third coordinate system (e.g., a certain point on the detector 112).

In some embodiments, the acquisition unit 810 may be connected to or communicate with the projection matrix unit 820, the deviation determination unit 830, the transformation determination unit 840, and/or the storage unit 850, and send data thereto.

The projection matrix unit 820 may determine a projection matrix of the first coordinate system and a source location based on the calibration data. For example, the projection matrix unit 820 may determine a projection matrix of the first coordinate system based on coordinates of the plurality of markers in the first coordinate system and the projection coordinates of the plurality of markers in the third coordinate system. Each projection matrix of the first coordinate system may correspond to one gantry angle. In some embodiments, the projection matrix unit 820 may determine a plurality of projection matrices of the first coordinate system. The plurality of projection matrices of the first coordinate system may include a first plurality of projection matrices of the first coordinate system and a second plurality of projection matrices of the first coordinate system. The projection matrix unit 820 may determine the second plurality of projection matrices of the first coordinate system based on the first plurality of projection matrices of the first coordinate system by way of, for example, interpolation, extrapolation.

The deviation determination unit 830 may determine a displacement and a rotation angle of the second coordinate system from the first coordinate system. In some embodiments, the deviation determination unit 830 may determine the displacement based on the plurality of source locations and the plurality of projection matrices of the first coordinate system. Merely by way of example, the deviation of the second coordinate system from the first coordinate system may include a first displacement of the second coordinate system from the first coordinate system in a first axis (e.g., the Y axis), a second displacement of the second coordinate system from the first coordinate system in a second axis (e.g, the X axis), and a third displacement of the second coordinate system from the first coordinate system in a third axis (e.g, the Z axis). An exemplary first displacement, second displacement, and/or third displacement can be seen in FIG. 7B. The deviation determination unit 830 may determine a rotation plane in the first coordinate system based on the plurality of source locations to determine the rotation angle. The rotation angle of the second coordinate system may include a first rotation angle of the $X_f$ axis of the second coordinate system with respect to the X axis of the first coordinate system, a second rotation angle of the $Y_f$ axis of the second coordinate system with respect to the Y axis of the first coordinate system, and a third rotation angle of the $Z_f$ axis of the second coordinate system with respect to the Z axis of the first coordinate system.

The deviation determination unit 830 may determine the second displacement and the third displacement based on the plurality of projection matrices of the first coordinate system. Further, the deviation determination unit 830 may determine the first displacement based on the rotation plane, the second displacement and the third displacement. Further, the displacement of the second coordinate system from the first coordinate system may be determined based on the first displacement, the second displacement, and the third displacement. In some embodiments, the deviation determination unit 830 may specify the displacement of the second coordinate system from the first coordinate system by specifying an origin coordinate of the second coordinate system (i.e., a coordinate of the origin of the second coordinate system) in the first coordinate system.

In some embodiments, the deviation determination unit 830 may be connected to or communicate with the projection matrix unit 820, the transformation determination unit 840, and/or the storage unit 850. Merely by way of example, the deviation determination unit 830 may send the origin coordinate of the second coordinate system in the first coordinate system and the rotation angle to the transformation determination unit 840.

The transformation determination unit 840 may determine a transformation matrix between the first coordinate system and the second coordinate system. For example, the transformation determination unit 840 may determine the transformation matrix based on the origin coordinate of the second coordinate system in the first coordinate system and the rotation angle. In some embodiments, the transformation determination unit 840 may further determine a plurality of projection matrices of the second coordinate system (also referred to as a first plurality of projection matrices of the second coordinate system) based on the plurality of projection matrices of the first coordinate system and the determined transformation matrix. Further, in some embodiments, the transformation determination unit 840 may determine a second plurality of projection matrices of the second coordinate system based on the first plurality of projection matrices of the second coordinate system by, for example, interpolation, extrapolation. In some embodiments, the transformation determination unit 840 may further determine the beam center ($u_0$, $v_0$) in the third coordinate system based on the projection matrix of the second coordinate system. In some embodiments, the projection location of the source 115 in the third coordinate system may vary when the source 115 rotates. The transformation determination unit 840 may determine the beam center in the third coordinate system based on a plurality of beam center values corresponding to a plurality of gantry angles. In some embodiments, the plurality of gantry angles may be equally-spaced, and the transformation determination unit 840 may determine the beam center ($u_0$, $v_0$) in the third coordinate system to be the mean of the plurality of beam center values. In some embodiments, the plurality of gantry angles may be unequally-spaced, and the transformation determination unit 840 may generate beam center values corresponding to equally-spaced gantry angles based on beam center values corresponding to unequally-spaced gantry angle by, for example, interpolating the beam center values corresponding to the unequally-spaced gantry angles. Further, the transformation determination unit 840 may generate the beam center ($u_0$, $v_0$) in the third coordinate system to be the mean of the generated beam center values.

The storage unit 850 may store data acquired from the acquisition unit 810, the projection matrix unit 820, the deviation determination unit 830, and/or the transformation determination unit 840. Exemplary data may include a plurality of source locations, the plurality of projection matrices, the origin coordinate of the second coordinate system in the first coordinate system, the transformation matrix, etc. In some embodiments, the storage unit 850 may store instructions and/or algorithms that may be executed by the projection matrix module 420 to perform the methods or processes (e.g., the process 900 and/or the process 1100) illustrated in the present disclosure. The storage unit 850 may be implemented via any storage device disclosed elsewhere in the present disclosure.

It should be noted that the above description of the projection matrix module 420 is merely provided for the purposes of illustration, and not intended to limit the scope of the present disclosure. For persons having ordinary skills in the art, multiple variations and modifications may be made under the teaching of the present invention. However, those variations and modifications do not depart from the scope of the present disclosure. For example, the deviation determination unit 830 rather than the acquisition unit 810 may be configured to determine the plurality of projection matrices of the first coordinate system. As another example, the storage unit 850 may be omitted and the function of the storage unit 850 may be realized by the storage module 440. As a further example, the projection matrix unit 820 may be omitted, and projection matrices of a coordinate system may be determined by a device (e.g., a device available at or provided by a manufacturer of the CT scanner 110 or the CT system 100) external to the projection matrix module 420 or external to the processing engine 140.

Figure 9A:
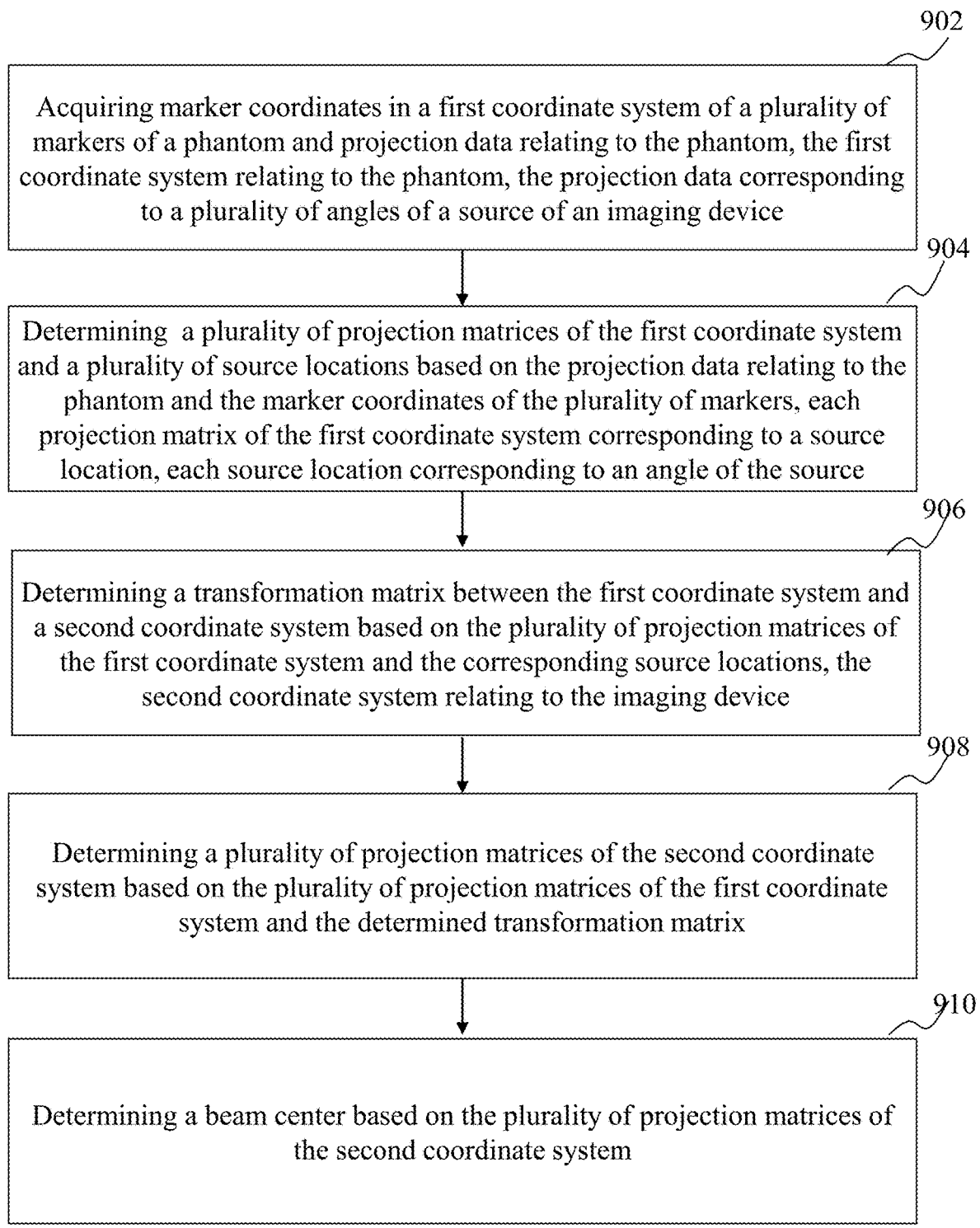
FIG. 9A is a flowchart illustrating an exemplary process for determining a plurality of projection matrices of the second coordinate system according to some embodiments of the present disclosure.

FIG. 9A is a flowchart illustrating an exemplary process 900 for determining a plurality of projection matrices of the second coordinate system according to some embodiments of the present disclosure. The process, or a portion thereof, may be implemented on a computing device as illustrated in FIG. 2 or a mobile device as illustrated in FIG. 3. For illustration purposes, the following description is provide with reference to the CT system 100 as illustrated in FIG. 1A and FIG. 1B. As already described, the CT system 100 includes a processing engine 140 including a projection matrix module 420 (as illustrated in FIG. 4).

In 902, marker coordinates in a first coordinate system of a plurality of markers of a phantom and projection data relating to the phantom may be acquired. The first coordinate system may relate to the phantom. The projection data may correspond to a plurality of angles of a source of an imaging device. The phantom may include a plurality of markers. For instance, the phantom may include at least 8 markers.

The marker coordinates in the first coordinate system and the projection data relating to the phantom may be acquired by the acquisition unit 810. The projection data relating to the phantom may be collected (e.g., by the detector 112 of the CT scanner 110) from a plurality of gantry angles. The plurality of markers of the phantom may include a first marker, a second marker, an ith marker, a nth marker, etc. As used herein, i or n may represent an integer larger than one. The position of the plurality of markers of the phantom may be registered, for example, by the projection matrix module 420, with the first coordinate system. The first coordinate system may be the coordinate system of the phantom. For example, the plurality of markers of the phantom may be assigned with one or more coordinates in the first coordinate system, based on the position of the plurality of markers of the phantom with respect to the origin of the first coordinate system (e.g., the center point of the phantom). The coordinates assigned to the plurality of markers may also be referred to as marker coordinates of the plurality of markers in the first coordinate system. The projection data relating to the phantom may be assigned, for example, by the projection matrix module 420, one or more coordinates in the third coordinate system relating to the detector 112 of the CT scanner 110, based on the position of the projection data (e.g., its corresponding position on the detector 112) with respect to the origin of the third coordinate system (e.g., a certain position on the detector 112). The coordinates assigned to the projection data relating to the plurality of markers of the phantom may also be referred to as a projection coordinate of the plurality of markers (of the phantom) in the third coordinate system. The projection data may correspond to a plurality of angles of a source of an imaging device. The projection data may be collected when the source of the imaging device is located at a plurality of gantry angles.

In 904, a plurality of projection matrices (or referred to as a first plurality of projection matrices) of the first coordinate system and a plurality of source locations may be determined based on the projection data relating to the phantom and the marker coordinates of the plurality of markers. A projection matrix of the first coordinate system may correspond to a source location that in turn, corresponds to an angle of the source. A source location may correspond to an angle (e.g., gantry angle) of the source 115. The source location may be determined by the projection matrix unit 820. The plurality of projection matrices of the first coordinate system may be determined by the projection matrix unit 820. The projection data relating to the phantom may include projection coordinates of the plurality of markers in the third coordinate system. In some embodiments, the plurality of projection matrices of the first coordinate system may be determined based on the coordinates of the plurality of markers in the first coordinate system and the projection coordinates of the plurality of markers in the third coordinate system. Merely by way of example, for a gantry angle, the projection matrix of the first coordinate system corresponding to the gantry angle may be determined by:

$$t_i \begin{bmatrix} u_i \\ v_i \\ 1 \end{bmatrix} = \begin{bmatrix} p_{11}x_i + p_{12}y_i + p_{13}z_i + p_{14} \\ p_{21}x_i + p_{22}y_i + p_{23}z_i + p_{24} \\ p_{31}x_i + p_{32}y_i + p_{33}z_i + p_{34} \end{bmatrix}, \quad (1)$$

where $(x_i, y_i, z_i)$ may represent the coordinate of the ith marker in the first coordinate system, $(u_i, v_i)$ may represent the projection coordinate of the ith marker in the third coordinate system, index i may be an integer larger than 1, and $t_i$ may represent a weight factor. Merely by way of example, the weight factor may relate to a penetration length of an X-ray emitted by the source 115 within the phantom.

The projection matrix of the first coordinate system may be further expressed as:

$$P = \begin{bmatrix} p_{11} & p_{12} & p_{13} & p_{14} \\ p_{21} & p_{22} & p_{23} & p_{24} \\ p_{31} & p_{32} & p_{33} & p_{34} \end{bmatrix}, \quad (2)$$

where P may represent the projection matrix of the first coordinate system, and each of $P_{11}$ through $P_{34}$ may represent an element of the projection matrix.

Additional projection matrices (or referred to as a second plurality of projection matrices) of the first coordinate system may be determined based on the first plurality of projection matrices of the first coordinate system by, for example, interpolation. Merely by way of example, the first plurality of projection matrices of the first coordinate system may include a first projection matrix corresponding to a first angle of the source, and a second projection matrix corresponding to a second angle of the source. A fourth projection matrix corresponding to a fourth angle of the source may be determined based on the first projection matrix and the second projection matrix by, e.g., interpolation. The fourth projection matrix may belong to the second plurality of projection matrices of the first coordinate system.

In 906, a transformation matrix between the first coordinate system and a second coordinate system may be determined based on at least some of the projection matrices of the first coordinate system and the corresponding source locations, the second coordinate system being relating to the imaging device. In some embodiments, the transformation matrix may be determined based on at least one of the first plurality of projection matrices of the first coordinate system determined based on the projection data relating to the phantom and the marker coordinates of the plurality of markers according to, for example, Equations (1) and (2). In some embodiments, the transformation matrix may be determined based on at least one of the first plurality of projection matrices of the first coordinate system and at least one of the second plurality of projection matricies of the first coordinate system, in which the second plurality of projection matrices may be determined based on the first plurality of projection matrices by, e.g., interpolation, extrapolation. In some embodiments, the transformation matrix may be determined based on at least one of the second plurality of projection matricies of the first coordinate system, in which the second plurality of projection matrices may be determined based on the first plurality of projection matrices by, e.g., interpolation, extrapolation.

The second coordinate system may relate to an imaging device. The second coordinate system may be an IEC fixed coordinate system of the CT system 100. Merely by way of example, the second coordinate system may include an $X_f$ axis, a $Y_f$ axis, and a $Z_f$ axis as illustrated in FIG. 7A. In some embodiments, the transformation matrix may be applied to transform information expressed in terms of the first coordinate system to information expressed in terms of the second coordinate system. Exemplary process for determining the transformation matrix may be illustrated in FIG. 9B.

In 908, a plurality of projection matrices of the second coordinate system may be determined based on the plurality of projection matrices of the first coordinate system and the determined transformation matrix. In some embodiments, the projection matrix of the second coordinate system may be determined by the transformation determination unit 840. A projection matrix of the second coordinate system may be determined based on a corresponding projection matrix of the first coordinate system and the determined transformation matrix. A projection matrix of the second coordinate system is considered corresponding to a projection matrix of the first coordinate system when they both correspond to a same gantry angle. Merely by way of example, the projection matrix of the second coordinate system may be determined by:

$$P_{IEC} = P \times T_{trans}, \quad (3)$$

wherein $P_{IEC}$ may represent the projection matrix of the second coordinate system.

In 910, a beam center may be determined based on the plurality of projection matrices of the second coordinate system. The beam center may be determined by the transformation determination unit 840. As used herein, the beam center may represent the projection location of the source in the third coordinate system. Merely by way of example, a plurality of projection matrices of the second coordinate system may be determined based on projection data of a phantom and coordinates of a plurality of markers of the phantom in the first coordinate system. Further, the projection coordinate of a source ($u_0$, $v_0$) in the third coordinate system may be determined based on the plurality of projection matrices of the second coordinate system. The beam center may be the coordinate of the detector unit on which the axis of the radiation beam emitted by the source 115 impinged on.

Figure 9B:
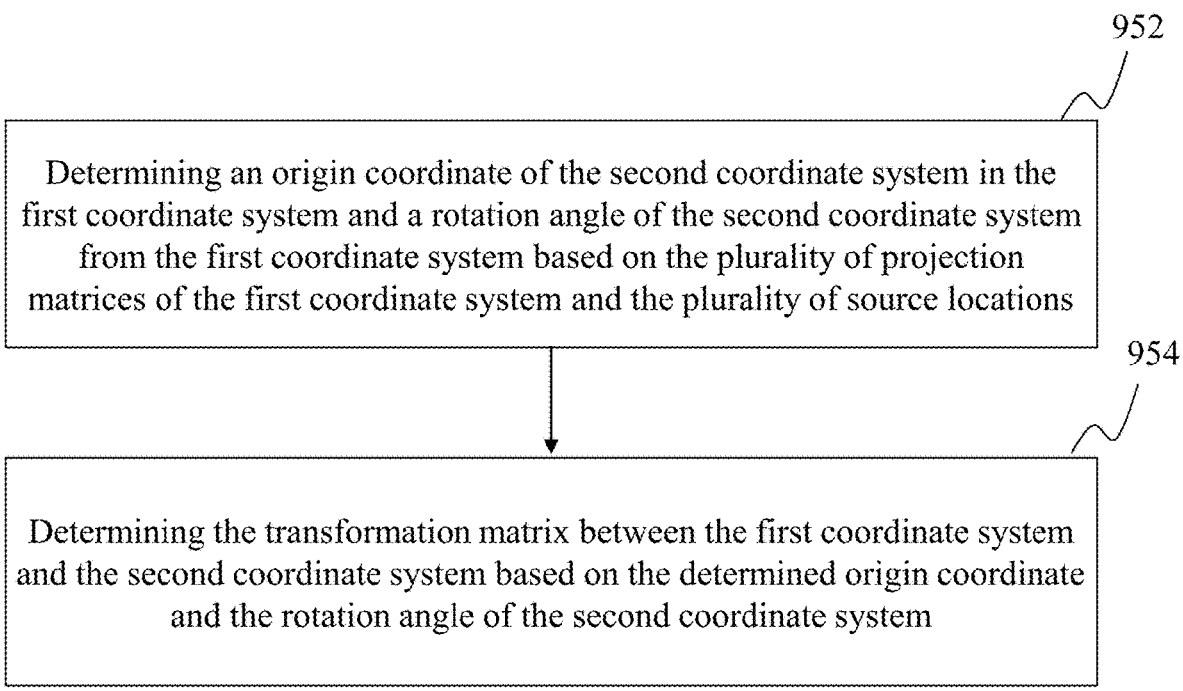
FIG. 9B is a flowchart illustrating an exemplary process for determining the transformation matrix between the first coordinate system and the second coordinate system according to some embodiments of the present disclosure.

FIG. 9B is a flowchart illustrating an exemplary process 950 for determining the transformation matrix between the first coordinate system and the second coordinate system according to some embodiments of the present disclosure. For illustration purposes, the following description is provide with reference to the CT system 100 as illustrated in FIG. 1A and FIG. 1B. As already described, the CT system 100 includes a processing engine 140 including a projection matrix module 420 (as illustrated in FIG. 4).

In 952, an origin coordinate of the second coordinate system in the first coordinate system and a rotation angle of the second coordinate system from the first coordinate system may be determined based on the plurality of projection matrices of the first coordinate system and the plurality of source locations. The origin coordinate of the second coordinate system in the first coordinate system may be determined based on the displacement of the origin of the second coordinate system from the origin of the first coordinate system. The displacement of the origin of the second coordinate system from the origin of the first coordinate system may include the first displacement in the Y axis, the second displacement in the X axis, and the third displacement in the Z axis. The second displacement and the third displacement may be determined based on the plurality of projection matrices of the first coordinate system. The first displacement may be determined based on the second displacement, the third displacement, and the rotation plane. The origin coordinate may be determined by the deviation determination unit 830. An exemplary process for determining the displacement of the second coordinate system from the first coordinate system may be found in FIG. 11 and the description thereof. The rotation angle may be determined by the deviation determination unit 830. The rotation angle of the second coordinate system may include a first rotation angle of the $X_f$ axis of the second coordinate system with respect to the X axis of the first coordinate system, a second rotation angle of the $Y_f$ axis of the second coordinate system with respect to the Y axis of the first coordinate system, and a third rotation angle of the $Z_f$ axis of the second coordinate system with respect to the Z axis of the first coordinate system.

In 954, the transformation matrix between the first coordinate system and the second coordinate system may be determined based on the determined origin coordinate and the rotation angle of the second coordinate system. The transformation matrix may be determined by the transformation determination unit 840. Merely by way of example, the transformation matrix may be expressed as:

$$T_{trans} = \begin{bmatrix} n_{x_1} & n_{y_1} & n_{z_1} & -x_0 \\ n_{x_2} & n_{y_2} & n_{z_2} & -y_0 \\ n_{x_3} & n_{y_3} & n_{z_3} & -z_0 \end{bmatrix}. \quad (4)$$

In equation (4), ($x_0$, $y_0$, $z_0$) may represent the origin coordinate of the second coordinate system in the first coordinate system. In some embodiments, the ($x_0$, $y_0$, $z_0$) may be determined by a process as illustrated below in FIG. 11. ($n_{x_1}$, $n_{x_2}$, $n_{x_3}$) may represent a first unit vector along the $X_f$ axis of the second coordinate system in the first coordinate system. ($n_{y_1}$, $n_{y_2}$, $n_{y_3}$) may represent a second unit vector along the $Y_f$ axis of the second coordinate system in the first coordinate system. ($n_{z_1}$, $n_{z_2}$, $n_{z_3}$) may represent a third unit vector along the $Z_f$ axis of the second coordinate system in the first coordinate system. $T_{trans}$ may represent the transformation matrix configured to, for example, transform information expressed in terms of the first coordinate system to information expressed in terms of the second coordinate system.

It should be noted that the above description of the flowchart in FIG. 9A and/or FIG. 9B is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, in FIG. 9A, an operation for storing the projection data may be added between 902 and 904.

Figure 10:
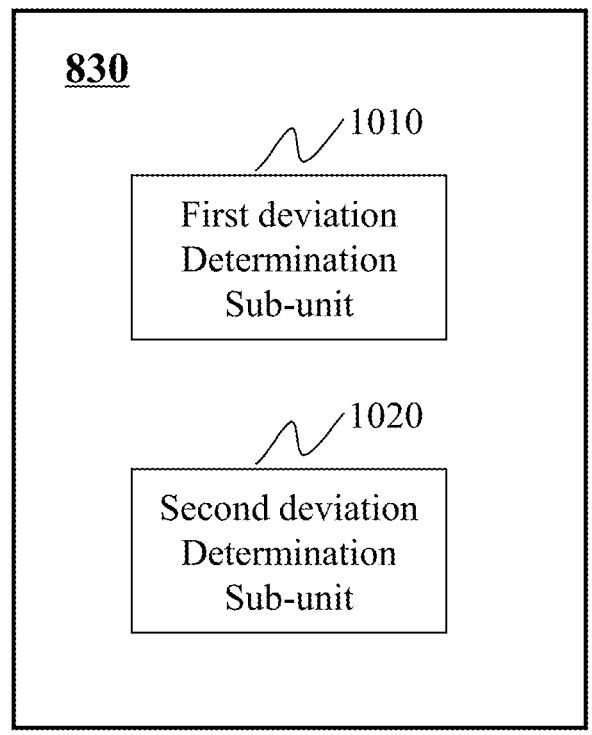
FIG. 10 is a block diagram illustrating an exemplary deviation determination unit according to some embodiments of the present disclosure.

FIG. 10 is a block diagram illustrating an exemplary deviation determination unit 830 according to some embodiments of the present disclosure. As illustrated in FIG. 10, the deviation determination unit 830 may include a first deviation determination sub-unit 1010 and a second deviation determination sub-unit 1020. The deviation determination unit 830, or a portion thereof, may be implemented on a computing device as illustrated in FIG. 2, or a mobile device as illustrated in FIG. 3.

The first deviation determination sub-unit 1010 may determine the rotation plane and the rotation angle of the second coordinate system from the first coordinate system. Merely by way of example, the first deviation determination sub-unit 1010 may determine a rotation plane based on the plurality of source locations, based on which the rotation angle may be determined. In some embodiments, the first deviation determination sub-unit 1010 may construct the rotation plane by minimizing a sum of squares of the distance from the plurality of source locations to the rotation plane.

The second deviation determination sub-unit 1020 may determine the first displacement, the second displacement and the third displacement of the second coordinate system from the first coordinate system. The second displacement may be in a second axis (e.g., X axis) of the first coordinate system, the third displacement may be in a third axis (e.g., Z axis) of the first coordinate system. In some embodiments, the second deviation determination sub-unit 1020 may determine the second displacement and the third displacement based on a plurality of projection matrices of the first coordinate system. Merely by way of example, the second deviation determination sub-unit 1020 may determine the second displacement and the third displacement by determining a sum of squares of deviation of the plurality of projection matrix elements from the mean of the plurality of projection matrix elements. Detailed description of the determination of the second displacement and the third displacement may be found elsewhere in the present disclosure. See, for example, the description of FIG. 11. A projection matrix element may be selected from a projection matrix of the first coordinate system. For a plurality of projection matrices of the first coordinate system, corresponding projection matrix elements (e.g., projection matrix elements having the same row and column indices in the plurality of projection matrices of the first coordinate system) may be selected. A projection matrix element may relate to the second displacement and the third displacement. The first displacement is in the first axis (e.g., Y axis) of the first coordinate system. The second deviation determination sub-unit 1020 may determine the first displacement based on the second displacement, the third displacement, and the rotation plane. Detailed description of the determination of the first displacement may be found elsewhere in the present disclosure. See, for example, the description of FIG. 11.

Figure 11:
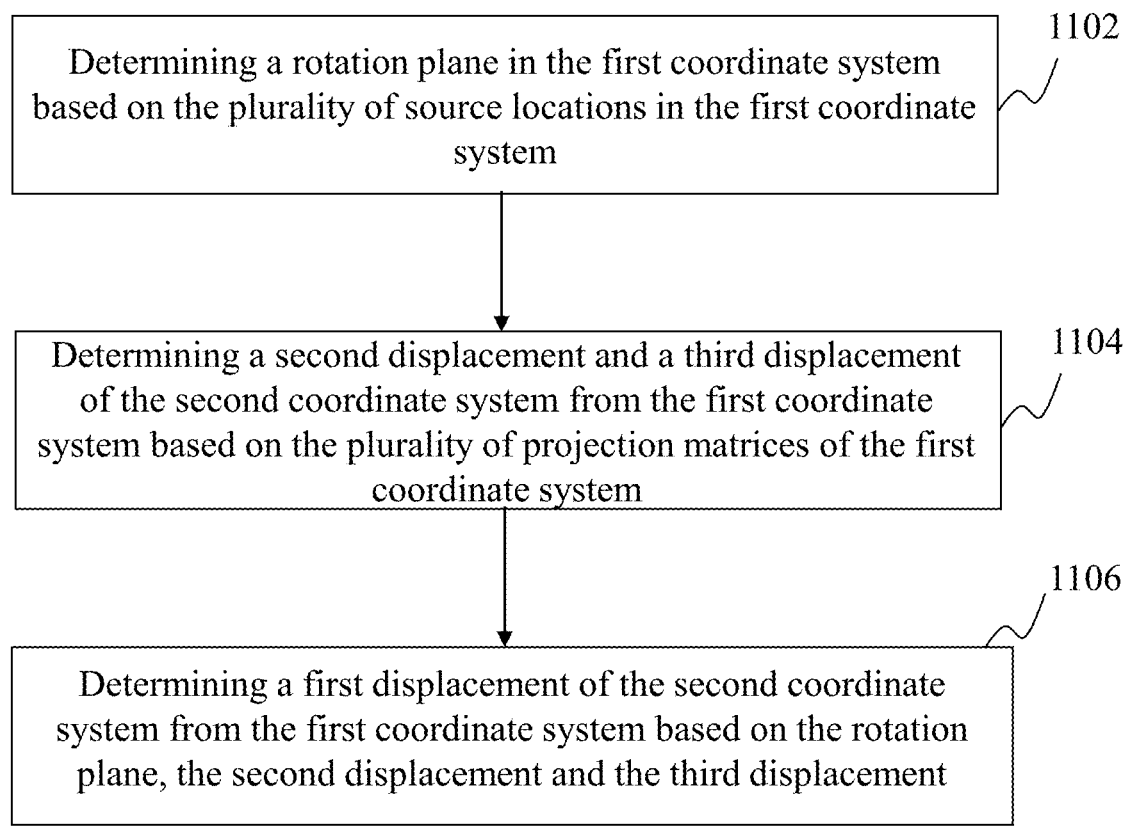
FIG. 11 is a flowchart illustrating an exemplary process for determining the deviation of the second coordinate system from the first coordinate system according to some embodiments of the present disclosure.

FIG. 11 is a flowchart illustrating an exemplary process 1100 for determining deviation of the second coordinate system from the first coordinate system according to some embodiments of the present disclosure. The process, or a portion thereof, may be implemented on a computing device as illustrated in FIG. 2 or a mobile device as illustrated in FIG. 3. For illustration purposes, the following description is provide with reference to the CT system 100 as illustrated in FIG. 1A and FIG. 1B. As already described, the CT system 100 includes a projection matrix module 420 including a deviation determination unit 830 (as illustrated in FIG. 8).

In 1102, a rotation plane in the first coordinate system may be constructed based on the plurality of source locations in the first coordinate system. The rotation plane may be constructed by the first deviation determination sub-unit 1010. Merely by way of example, the rotation plane may be constructed based on:

$$\min \sum_{\theta=0}^{2\pi} (n_{y_1} x + n_{y_2} y + n_{y_3} z + d_0)^2, \quad (5)$$

where (x, y, z) may represent the source location of each gantry angle in the first coordinate system, $(n_{y_1}, n_{y_2}, n_{y_3}, d_0)$ may represent the rotation plane in the first coordinate system, $(n_{y_1}, n_{y_2}, n_{y_3})$ may represent a normal vector of the rotation plane, and $d_0$ may represent an intercept of the rotation plane.

In 1104, a second displacement and a third displacement of the second coordinate system from the first coordinate system may be determined based on the plurality of projection matrices of the first coordinate system. The second displacement and a third displacement may be determined by the second deviation determination sub-unit 1020.

In some embodiments, the second displacement and a third displacement may be determined by:

$$u_\theta = u_0 - \frac{f}{p_w D}(z_0 \sin\theta - x_0 \cos\theta), \quad (6)$$

where f may represent a source-image distance (SID), pw may represent a width of a detector unit (e.g., a width of a pixel), D may represent a source-axis distance (SAD), $(u_0, v_0)$ may represent the source location in the third coordinate system, and $X_0$ and $z_0$ may represent the second displacement and the third displacement, respectively.

As illustrated in equation (6), $u_\theta$ in the first coordinate system may include two factors: an intrinsic panel movement $u_0$ and an additional shift. The additional shift may be caused by, for example, a phantom displacement. The intrinsic panel movement $u_0$ may be mainly caused by, for example, gravity. In some embodiments, as gravity is the main cause of intrinsic panel movement, the panel movement may be symmetrical in the whole rotation and return to its original position after the gantry rotates 360 degrees. Thus, even after phantom displacement, the mean value of $u_\theta$ in an even distributed rotation is not changed. Thus, the above information may be used to calculate the second displacement $x_0$ and third displacement $z_0$.

The $x_0$ and $z_0$ may be determined by minimizing the following problems where $u_\theta$ is determined by the equation (6):

$$\min_{x_0, z_0} \sum_{\theta=0}^{2\pi} (u_\theta - \overline{u})^2, \quad (7)$$

where $\overline{u}$ may represent a mean value (or an average value) of $u_\theta$ The initial value of $u_\theta$ may be the projection matrix element of the projection matrix of the first coordinate system (e.g., P14) corresponding to the gantry angle θ.

In 1106, a first displacement of the second coordinate system from the first coordinate system may be determined based on the rotation plane, the second displacement and the third displacement. As rotation plane is known and displacement in X and Z direction is also calculated from above procedures, we can calculate the displacement in Y direction by simple equation:

$$y_0 = -(n_{x2}x_0 + n_{z2}z_0 + d_0)/n_{y2}. \qquad (8)$$

It should be noted that the above description of the flowchart in FIG. 11 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, a step for storing the rotation plane may be added between step 1102 and step 1104.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on at least one machine that is associated with an imaging device, each of the at least one machine has at least one processor and storage storing a set of instructions, the method comprising:
    acquiring, by the at least one machine, a marker coordinate in a first coordinate system of at least one marker of a phantom, the first coordinate system relating to the phantom including the at least one marker;
    for each angle of a first plurality of angles of a source of an imaging device,
        obtaining, by the at least one machine, from the imaging device, projection data relating to the phantom when the source of the imaging device is located at the angle; and
        determining, by the at least one machine, based on the projection data and the marker coordinate of the at least one marker of the phantom, a source location corresponding to the angle of the source of the imaging device and a projection matrix of the first coordinate system corresponding to the angle;
    determining, by the at least one machine, a transformation matrix between the first coordinate system and a second coordinate system based on at least one projection matrix of a first plurality of projection matrices of the first coordinate system and the at least one corresponding source location, the first plurality of projection matrices of the first coordinate system corresponding to the first plurality of angles of the source, the second coordinate system relating to the imaging device;
    determining, by the at least one machine, a first plurality of projection matrices of the second coordinate system based on the at least one projection matrix of the first plurality of projection matrices of the first coordinate system and the determined transformation matrix, a projection matrix of the second coordinate system corresponding to an angle of the source; and
    generating an image of an object by processing the projection data relating to the object with the first plurality of projection matrices.

2. The method of claim 1, wherein the determining a transformation matrix between the first coordinate system and a second coordinate system comprises:
    determining, by the at least one machine, an origin coordinate of the second coordinate system in the first coordinate system and a rotation angle of the second coordinate system from the first coordinate system based on the first plurality of projection matrices of the first coordinate system and the corresponding source locations, the origin coordinate of the second coordinate system in the first coordinate system being defined by a first displacement, a second displacement, and a third displacement from the origin of the first coordinate system; and
    determining, by the at least one machine, the transformation matrix between the first coordinate system and the second coordinate system based on the determined origin coordinate of the second coordinate system and the rotation angle.

3. The method of claim 2, wherein the first coordinate system comprises a first axis, a second axis, and a third axis, the determining an origin coordinate of the second coordinate system in the first coordinate system and a rotation angle of the second coordinate system from the first coordinate system comprises:
    determining, by the at least one machine, a rotation plane in the first coordinate system based on the plurality of source locations corresponding to the first plurality of angles of the source;
    determining, by the at least one machine, the rotation angle of the second coordinate system from the first coordinate system based on the rotation plane;
    determining, by the at least one machine, the second displacement and the third displacement of the second coordinate system from the first coordinate system based on the first plurality of projection matrices of the first coordinate system, the second displacement being in the second axis of the first coordinate system, the third displacement being in the third axis of the first coordinate system; and
    determining, by the at least one machine, the first displacement based on the second displacement, the third displacement, and the rotation plane, the first displacement being in the first axis of the first coordinate system.

4. The method of claim 1, wherein the determining the projection matrix of the first coordinate system when the source of the imaging device is located at the angle of the source corresponding to the source location comprises:
    determining, by the at least one machine, in a third coordinate system, a projection coordinate of the at least one marker of the phantom, the third coordinate system being an image coordinate system of the imaging device; and
    determining, by the at least one machine, the projection matrix of the first coordinate system based on the marker coordinate in the first coordinate system and the projection coordinate in the third coordinate system.

5. The method of claim 4, further comprising:
acquiring, by the imaging device, projection data related to a subject; and
processing the projection data related to the subject with the projection matrices of the second coordinate system to generate an image.

6. The method of claim 1, wherein the determining a projection matrix of the second coordinate system comprises:
multiplying, by the at least one machine, the projection matrix of the first coordinate system with the determined transformation matrix, the determined transformation matrix being configured to transform the first coordinate system to the second coordinate system.

7. A system, comprising:
at least one storage medium including a set of instructions; and
at least one processor configured to communicate with the at least one storage medium, wherein when executing the set of instructions, the at least one processor is directed to:
acquire, from an imaging device, projection data of a phantom comprising a plurality of markers at a plurality of angles of a source of the imaging device;
determine, based on the projection data of the phantom and coordinates of the plurality of markers in a first coordinate system, a plurality of projection matrices of the first coordinate system and a transformation matrix between the first coordinate system and a second coordinate system, an angle of the source corresponding to a projection matrix of the first coordinate system, the first coordinate system relating to the phantom, and the second coordinate system relating to the imaging device;
determine a plurality of projection matrices of the second coordinate system based on the plurality of projection matrices of the first coordinate system and the transformation matrix between the first coordinate system and a second coordinate system, a projection matrix of the second coordinate system corresponding to an angle of the source; and
store the plurality of the determined projection matrices of the second coordinate system as an electronic file.

8. The system of claim 7, wherein the at least one processor is further configured to:
determine a projection coordinate of the source in a third coordinate system based on the plurality of projection matrices of the second coordinate system, the third coordinate system being an image coordinate system of the imaging device.

9. The system of claim 7, wherein the at least one processor is further configured to:
determine, based on the projection data of the phantom and the coordinates of the markers in the first coordinate system; a plurality of source locations, a source location corresponding to an angle of the source;
determine an origin coordinate of the second coordinate system in the first coordinate system and a rotation angle of the second coordinate system from the first coordinate system based on the plurality of projection matrices of the first coordinate system and the corresponding source locations, the origin coordinate of the second coordinate system in the first coordinate system being defined by a first displacement, a second displacement, and a third displacement from the origin of the first coordinate system; and determine the transformation matrix between the first coordinate system and the second coordinate system based on the determined origin coordinate of the second coordinate system and the rotation angle.

10. The system of claim 9, wherein the at least one processor is further configured to:
determine a rotation plane in the first coordinate system based on the plurality of source locations;
determine the rotation angle of the second coordinate system from the first coordinate system based on the rotation plane;
determine the second displacement and the third displacement of the second coordinate system from the first coordinate system based on the plurality of projection matrices of the first coordinate system, the second displacement being in the second axis of the first coordinate system, the third displacement being in the third axis of the first coordinate system; and
determine the first displacement based on the second displacement, the third displacement, and the rotation plane, the first displacement being in the first axis of the first coordinate system.

11. The system of claim 10, wherein to determine a rotation plane in the first coordinate system, the at least one processor is configured to:
construct the rotation plane by minimizing a sum of squares of the distance from the plurality of source locations corresponding to the plurality of angles of the source, to the rotation plane.

12. The system of claim 10, wherein to determine a second displacement and a third displacement, the at least one processor is further configured to:
for each projection matrix of the plurality of the projection matrices of the first coordinate system, determine a projection matrix element in the projection matrix of the first coordinate system, the projection matrix element relating to the second displacement and the third displacement;
determine a mean of the plurality of projection matrix elements; and
determine the second displacement and the third displacement by minimizing a sum of squares of deviations of the plurality of projection matrix elements from the mean of the plurality of projection matrix elements.

13. The system of claim 10, wherein the plurality of angles of the source include a first angle of the source, a second angle of the source different from the first angle of the source, and a third angle of the source different from the first angle of the source and the second angle of the source.

14. The system of claim 13, wherein a first angle difference between the first angle of the source and the second angle of the source or a second angle difference between the second angle of the source and the third angle of the source ranges from 0 degree to 20 degrees.

15. The system of claim 13, wherein the plurality of projection matrices of the first coordinate system include a first projection matrix corresponding to the first angle of the source, and a second projection matrix corresponding to the second angle of the source.

16. The system of claim 7, wherein the at least one processor is further configured to generate projection matrices corresponding to equally-spaced angles of the source based on a plurality of projection matrices corresponding to unequally-spaced angles of the source.

17. The system of claim 7, wherein the at least one processor is further configured to:

determine, based on at least one projection matrix of a plurality of projection matrices of the first coordinate system and the at least one corresponding source location, a second plurality of projection matrices of the first coordinate system and a second plurality of corresponding source locations, a projection matrix of the second plurality of projection matrices corresponding to a source location that in turn corresponds to an angle of a second plurality of angles of the source; and determine, based on at least one projection matrix of the second plurality of projection matrices of the first coordinate system and the determined transformation matrix, at least one projection matrix of a plurality of projection matrices of the second coordinate system.

18. The system of claim 17, wherein the second plurality of angles of the source include a fourth angle of the source, and to determine a second plurality of projection matrices of the first coordinate system, the at least one processor is further configured to:

determine a fourth projection matrix corresponding to a fourth angle of the source by interpolating the first projection matrix and the second projection matrix.

19. The system of claim 17, wherein the at least one processor is further configured to:

determine the transformation matrix between the first coordinate system and a second coordinate system based further on at least one projection matrix of the second plurality of projection matrices of the first coordinate system and the at least one corresponding source location.

20. A method implemented on at least one machine that is associated with an imaging device, each of the at least one machine has at least one processor and storage storing a set of instructions, the method comprising:

acquiring, by the at least one machine, from an imaging device, projection data of a phantom comprising a plurality of markers, determining, by the at least one machine, based on the projection data of the phantom and coordinates of the plurality of markers in a first coordinate system, a plurality of projection matrices of a second coordinate system, the first coordinate system being a coordinate system of the phantom, and the second coordinate system being a coordinate system of the imaging device; and determining, by the at least one machine, based on the plurality of projection matrices of the second coordinate system, a projection coordinate of a source of the imaging device in a third coordinate system, the third coordinate system being an image coordinate system of the imaging device.

* * * * *